US012357548B2

(12) United States Patent
Yang et al.

(10) Patent No.: US 12,357,548 B2
(45) Date of Patent: Jul. 15, 2025

(54) SUNSCREEN FORMULATIONS COMPRISING AN OLEOSOME SUSPENSION AND AN ACIDIC BUFFERING SYSTEM

(71) Applicant: BOTANECO INC., Calgary (CA)

(72) Inventors: Soo In Yang, Calgary (CA); Shuanghui Liu, Calgary (CA); Geoffrey Brooks, Reno, NV (US); Yves Lanctot, Deux-Montagnes (CA)

(73) Assignee: BOTANECO INC., Calgary (CA)

( * ) Notice: Subject to any disclaimer, the term of this patent is extended or adjusted under 35 U.S.C. 154(b) by 149 days.

(21) Appl. No.: 16/092,750

(22) PCT Filed: Apr. 13, 2017

(86) PCT No.: PCT/CA2017/050459
§ 371 (c)(1),
(2) Date: Oct. 10, 2018

(87) PCT Pub. No.: WO2017/177334
PCT Pub. Date: Oct. 19, 2017

(65) Prior Publication Data
US 2019/0105248 A1 Apr. 11, 2019

Related U.S. Application Data

(60) Provisional application No. 62/322,941, filed on Apr. 15, 2016.

(51) Int. Cl.
| | |
|---|---|
| *A61K 8/14* | (2006.01) |
| *A61K 8/35* | (2006.01) |
| *A61K 8/37* | (2006.01) |
| *A61K 8/92* | (2006.01) |
| *A61Q 17/04* | (2006.01) |

(52) U.S. Cl.
CPC .................. *A61K 8/14* (2013.01); *A61K 8/35* (2013.01); *A61K 8/37* (2013.01); *A61K 8/922* (2013.01); *A61Q 17/04* (2013.01)

(58) Field of Classification Search
CPC ... A61K 8/14; A61K 8/35; A61K 8/37; A61K 8/922; A61Q 17/04
See application file for complete search history.

(56) References Cited

U.S. PATENT DOCUMENTS

| | | | |
|---|---|---|---|
| 6,183,762 B1 | 2/2001 | Deckers et al. | |
| 8,343,945 B2 | 1/2013 | Tamarkin et al. | |
| 2007/0292359 A1 | 12/2007 | Friedman et al. | |
| 2008/0241082 A1* | 10/2008 | Guth | A61Q 19/00 424/59 |
| 2010/0172944 A1* | 7/2010 | Laboureau | A61K 8/585 424/59 |
| 2011/0081386 A1* | 4/2011 | Guth | A61K 8/86 424/400 |
| 2011/0124543 A1 | 5/2011 | Lutrario et al. | |
| 2015/0366784 A1* | 12/2015 | Ramirez | A61K 8/345 424/59 |

FOREIGN PATENT DOCUMENTS

| | | |
|---|---|---|
| CA | 2590607 C | 10/2005 |
| WO | 00/30602 A1 | 6/2000 |
| WO | 2005/097059 A1 | 10/2005 |
| WO | 2009/126301 A2 | 10/2009 |
| WO | 2009/126302 A2 | 10/2009 |

OTHER PUBLICATIONS

Extended European Search Report received for Application No. 17781687.3, mailed on Nov. 18, 2019, 09 pages.
Mintel, "Dynamic Skin Recovery SPF 50", GNPD, Database Accession No. 2593573, Sep. 1, 2014, 06 pages.
Mintel, "Protection 50 Sport SPF 50", GNPD, Database Accession No. 2387503, May 20, 2014, 05 pages.
International Search Report and Written Opinion mailed Aug. 8, 2017 in International Application No. PCT/CA2017/050459, filed Apr. 13, 2017.
D. Tang, J. Guth, J. Soc. Cosmet. Scientists Korea (2006), vol. 32, No. 3, p. 149-152.

* cited by examiner

*Primary Examiner* — Aradhana Sasan
(74) *Attorney, Agent, or Firm* — Billion & Armitage

(57) ABSTRACT

Methods for making an oleosome-based sunscreen formulation are provided. The methods involve preparing an oleosome suspension buffered at a pH in a range from about pH 3 to about pH 6, and contacting the oleosome formulation with a sunscreen active agent to prepare a sunscreen formulation. The sunscreen formulation may be used to prepare personal care products capable of protecting human skin against ultraviolet radiation. Related compositions are also provided.

24 Claims, 9 Drawing Sheets

SUNSCREEN FORMULATIONS COMPRISING AN OLEOSOME SUSPENSION AND AN ACIDIC BUFFERING SYSTEM

RELATED APPLICATION

This Application is a National Stage entry of International Application PCT/CA2017/050459, filed Apr. 13, 2017, which claims the priority benefit of U.S. Provisional Application No. 62/322,941, filed Apr. 15, 2016, each of which is incorporated herein in its entirety by reference for all purposes.

FIELD OF THE DISCLOSURE

The present disclosure relates to ingredients for use in the formulation of personal care products, and notably to sunscreen active ingredients for use in the formulation of personal care products.

BACKGROUND OF THE DISCLOSURE

The following paragraphs are provided by way of background to the present disclosure. They are not however an admission that anything discussed therein is prior art or part of the knowledge of persons skilled in the art.

Solar ultraviolet (UV) radiation having a wavelength between 200 nm and 400 nm is commonly further classified into three regions: from 320 to 400 nm (UV-A), 290 to 320 nm (UV-B) and from 200 to 290 nm (UV-C). UV-C radiation is largely absorbed by the ozone layer of the earth's atmosphere. However exposure of the skin to UV-A and UV-B radiation can result in skin reddening and skin burns. Moreover prolonged exposure to UV-A and UV-B radiation can lead to the development of more serious skin disorders, such as light dermatoses and erythemata, as well as increase the risk of skin cancers, including melanoma, and accelerate skin aging, for example, as a result of loss of skin elasticity and skin wrinkling. It is therefore well understood that sunscreen compositions capable of shielding the body from UV-A and UV-B radiation, and techniques of making such compositions are highly desirable. Nevertheless, although a plethora of sunscreen compositions has evolved, numerous shortcomings associated with known sunscreen compositions remain.

In order to evaluate the level of protection the skin receives when exposed to UV-A and UV-B radiation, sunscreen compositions are commonly assayed by measuring the sun protection factor (SPF) of the composition. Manufacturers of personal care products attempt to provide consumers with sunscreen products having high SPFs. One manner of achieving this is by incorporating high concentrations of UV-A and UV-B sunscreen active ingredients in sunscreen products. However above certain concentrations, safety and regulatory limitations can become prohibitive. Furthermore, at high concentrations, sunscreen actives are known to cause irritation, which is a particularly a concern when the sunscreen composition is applied to the facial area, where eye irritation can readily occur. Sensory properties and aesthetics of sunscreen products can also be affected by the incorporation of high concentrations of sunscreen agents. One further drawback of this approach is the cost associated with the incorporation of high concentrations of sunscreen active ingredients, which are expensive. Hence, there remains a problem in the art with providing personal care formulations exhibiting high SPFs and desirable sensory and aesthetic attributes, while having relatively low quantities of sunscreen actives in the compositions.

Accordingly, there remains a need in the art for novel sunscreen compositions and techniques of making such compositions.

SUMMARY OF THE DISCLOSURE

The following paragraphs are intended to introduce the reader to the more detailed description that follows and not to define or limit the claimed subject matter of the present disclosure.

In one aspect, the present disclosure relates to personal care products comprising sunscreen active ingredients, and methods of making such products.

In another aspect, the present disclosure relates to ingredients used in the formulation of personal care products, including, but not limited to, sunscreen active ingredients and oleaginous ingredients, notably plant oleosomes.

Accordingly, the present disclosure provides, in least one embodiment, a method of preparing a sunscreen formulation comprising:
providing a sunscreen active ingredient;
preparing an oleosome suspension buffered at a pH from about pH 3 to about pH 6;
contacting the oleosome suspension with the sunscreen active ingredient at a pH of from about pH 3 to about pH 6 to form a sunscreen formulation.

In some embodiments, the oleosome suspension is buffered using a buffering system comprising a weak acid.

In some embodiments, the oleosome suspension is buffered using a weak acid comprising a pKa of from about 3 to about 6.

In some embodiments, the oleosome suspension is buffered using a buffering system comprising a strong base.

In some embodiments, the oleosome suspension is buffered using a buffering system comprising a weak acid and a strong base.

In some embodiments, the oleosome suspension is buffered using a citrate-sodium hydroxide buffering system.

In some embodiments, the oleosome suspension is buffered using a malic acid sodium hydroxide buffering system.

In some embodiments, the oleosome suspension is buffered using a citric acid potassium hydroxide buffering system.

In some embodiments, the oleosome suspension is buffered using an acetic acid potassium hydroxide buffering system.

In some embodiments, the oleosome suspension is buffered using a malic acid potassium hydroxide buffering system.

In some embodiments, the buffering capacity of the oleosome suspension within the pH range of from about pH 3 to about pH 6 is at least 0.1.

In some embodiments, the sunscreen active is contacted with the oleosome suspension at a pH in the range of from about pH 4.0 to about pH 5.0.

In some embodiments, the SPF rate of the sunscreen formulation is at least SPF 15.

In some embodiments, the SPF rate of the sunscreen formulation is at least SPF 30.

In some embodiments, the sunscreen formulation is further formulated with at least one diluent, excipient or carrier.

The present disclosure further provides, in at least one embodiment, a sunscreen formulation buffered to a pH from about pH 3 to about pH 6 comprising or consisting of a sunscreen active ingredient and an oleosome suspension.

In some embodiments, the sunscreen formulation comprises an oleosome suspension, a sunscreen active ingredient, one or more buffering agents and water, which together constitute at least 90% (w/w), at least 95% (w/w), at least 96% (w/w), at least 97% (w/w), at least 98% (w/w), or at least 99% (w/w) of the sunscreen formulation.

In some embodiments, the formulation comprises an oleosome suspension buffered using a buffering system comprising a weak acid.

In some embodiments, the formulation comprises a weak acid comprising a pKa of from about 3 to about 6.

In some embodiments, the formulation comprises an oleosome suspension buffered using a buffering system comprising a strong base.

In some embodiments, the formulation comprises an oleosome suspension buffered using a buffering system comprising a weak acid and a strong base.

In some embodiments, the formulation comprises a weak acid comprising citric acid and sodium hydroxide.

In some embodiments, the formulation comprises a weak acid comprising acetic acid and sodium hydroxide.

In some embodiments, the formulation comprises a weak acid comprising malic acid and sodium hydroxide.

In some embodiments, the formulation comprises a weak acid comprising citric acid and potassium hydroxide.

In some embodiments, the formulation comprises a weak acid comprising acetic acid and potassium hydroxide.

In some embodiments, the formulation comprises a weak acid comprising malic acid and potassium hydroxide.

In some embodiments, the formulation comprises an oleosome suspension having a buffering capacity within the pH range of from about pH 3 to about pH 6 is at least 0.1.

In some embodiments, the SPF rate of the sunscreen formulation is at least SPF 15.

In some embodiments, the SPF rate of the sunscreen formulation is at least SPF 30.

The present disclosure further provides, in at least one embodiment, a method of preparing a personal care product comprising a sunscreen active ingredient, the method comprising:
  providing a sunscreen formulation buffered to a pH from about pH 3 to about pH 6 comprising a sunscreen active ingredient and an oleosome suspension;
  formulating the sunscreen formulation with at least one ingredient suitable for the
  preparation of a personal care product to form a personal care product comprising a sunscreen active ingredient.

In some embodiments, the method comprises adjusting the pH to obtain a personal care product having a pH of at least pH 5.5.

In some embodiments, the method comprises using an oleosome suspension that is buffered using a buffering system comprising a weak acid.

In some embodiments, the method comprises using an oleosome suspension that is buffered using a weak acid comprising a pKa of from about 3 to about 6.

In some embodiments, the method comprises using an oleosome suspension that is buffered using a buffering system comprising a strong base.

In some embodiments, the method comprises using an oleosome suspension that is buffered using a buffering system comprising a weak acid and a strong base.

In some embodiments, the method comprises using an oleosome suspension that is buffered using citric acid as the weak acid and sodium hydroxide as the strong base.

In some embodiments, the method comprises using an oleosome suspension that is buffered using acetic acid as the weak acid and sodium hydroxide as the strong base.

In some embodiments, the method comprises using an oleosome suspension that is buffered using malic acid as the weak acid and sodium hydroxide as the strong base.

In some embodiments, the method comprises using an oleosome suspension that is buffered using citric acid as the weak acid and potassium hydroxide as the strong base.

In some embodiments, the method comprises using an oleosome suspension that is buffered using acetic acid as the weak acid and potassium hydroxide as the strong base.

In some embodiments, the method comprises using an oleosome suspension that is buffered using malic acid as the weak acid and potassium hydroxide as the strong base.

In some embodiments, the method comprises using an oleosome suspension wherein the buffering capacity of the oleosome suspension within the pH range of from about pH 3 to about pH 6 is at least 0.1.

In some embodiments, the method comprises using a sunscreen formulation the SPF rate of the sunscreen formulation is at least SPF 15.

In some embodiments, the method comprises using a sunscreen formulation the SPF rate of the sunscreen formulation is at least SPF 30.

In some embodiments, the method comprises formulating a personal care product wherein the SPF rate of the personal care product is at least SPF 2.

In some embodiments, the at least one additional ingredient is a diluent, excipient or carrier.

In some embodiments, the formulating further comprises adjusting the pH to obtain a personal care product having a pH of at least 5.0, 5.5, 6.0, 6.5, 7.0, 7.5 or 8.5.

The present disclosure further provides in at least one embodiment, a method of preparing a personal care product comprising a sunscreen active ingredient, the method comprising:
  providing a sunscreen active ingredient;
  preparing an oleosome suspension buffered at a pH of about pH 3 to about pH 6;
  contacting the oleosome suspension with the sunscreen active ingredient to form a sunscreen formulation; and
  formulating the sunscreen formulation with at least one ingredient suitable for the preparation of a personal care product to form a personal care product comprising the sunscreen active ingredient.

In some embodiments, the at least one additional ingredient is a diluent, excipient or carrier.

In some embodiments, the personal care product exhibits a UV protection rate of at least SPF 15.

In some embodiments, the personal care product exhibits a UV protection rate of at least SPF 30.

In some embodiments, the pH of the personal care product ranges from a pH of about pH 5.5 to about pH 8.5.

In some embodiments, the sunscreen active agent constitutes from about 0.1% (w/w) to about 10% (w/w) of the personal care product.

In some embodiments, the personal care product is selected from the group consisting of skincare products, hair care products, bath and body wash products, lip care products, and make-up products.

The present disclosure further provides in at least one embodiment a personal care product formulated using a sunscreen active agent and oleosome suspension buffered to a pH from about pH 3 to about pH 6.

In some embodiments, the personal care product comprises the sunscreen formulation together with a diluent, excipient or carrier.

In some embodiments, the personal care product exhibits a UV protection rate of at least SPF 15.

In some embodiments, the personal care product exhibits a UV protection rate of at least SPF 30.

In some embodiments, the pH of the personal care product ranges from a pH of about pH 5.5 to about pH 8.5.

In some embodiments, the sunscreen active agent constitutes from about 0.1% (w/w) to about 10% (w/w) of the personal care product.

In some embodiments, the personal care product is selected from the group consisting of skincare products, hair care products, bath and body wash products, lip care products, and make-up products.

The present disclosure further provides, in at least one embodiment a use of a sunscreen formulation buffered to a pH from about pH 3 to about pH 6 comprising or consisting of a sunscreen active ingredient and an oleosome suspension to prepare a personal care product.

Other features and advantages or the present disclosure will become apparent from the following detailed description. It should be understood, however, that the detailed description, while indicating preferred implementations of the present disclosure, are given by way of illustration only, since various changes and modification within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figure. The figure provided herein is provided for a better understanding of the example embodiments and to show more clearly how the various embodiments may be carried into effect. The figure is not intended to limit the present disclosure.

DETAILED DESCRIPTION OF THE DISCLOSURE

Figure 1:
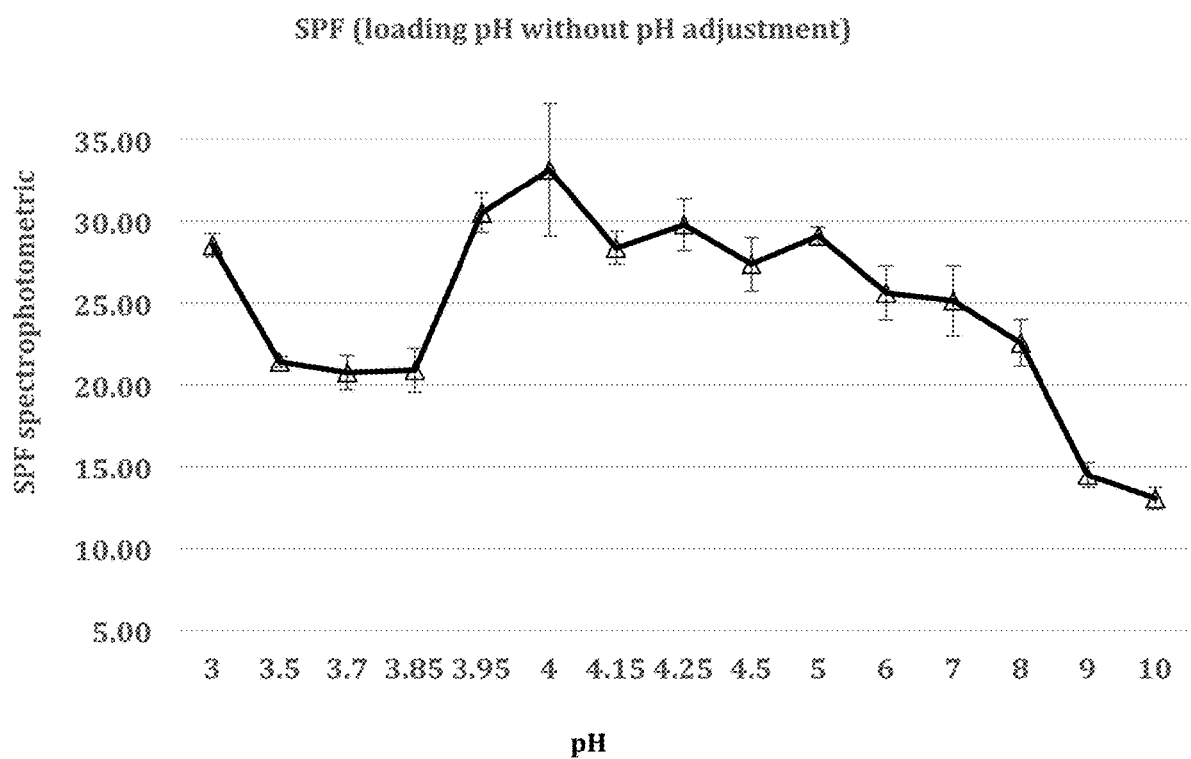
FIG. 1 is a graph representing certain results obtained in the making and using of an embodiment of a sunscreen formulation of the present disclosure. The graph shows SPF-rates of a personal care product comprising a sunscreen formulation as a function of pH of the sunscreen formulation.

Various compositions and methods will be described below to provide an example of an embodiment of each claimed subject matter. No embodiment described below limits any claimed subject matter and any claimed subject matter may cover methods, processes, or compositions that differ from those described below. The claimed subject matter is not limited to compositions or methods having all of the features of any one composition, method, or process described below or to features common to multiple or all of the compositions, or methods described below. It is possible that a composition, method or process described below is not an embodiment of any claimed subject matter. Any subject matter disclosed in a composition, method or process described below that is not claimed in this document may be the subject matter of another protective instrument, for example, a continuing patent application, and the applicants, inventors or owners do not intend to abandon, disclaim or dedicate to the public any such subject matter by its disclosure in this document.

All publications, patents, and patent applications are herein incorporated by reference in their entirety to the same extent as if each individual publication, patent or patent application was specifically and indicates to be incorporated by reference in its entirety. These publications, patents and patent applications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

As used herein and in the claims, the singular forms include the plural reference and vice versa unless the context clearly indicates otherwise.

Throughout this specification, unless otherwise indicated, "comprise," "comprises" and "comprising" are used inclusively rather than exclusively, so that a stated integer or group of integers may include one or more other non-stated integers or groups of integers.

Definitions

"*Carthamus*", as used herein, refers to a plant belonging to the biological genus *Carthamus* and includes, without limitation, the species *Carthamus tinctorius*, also known as safflower, *Carthamus alexandrinus, Carthamus arborescens, Carthamus baeticus, Carthamus creticus, Carthamus flavescens, Carthamus glaucus, Carthamus lanatus, Carthamus leucocautos, Carthamus oxyacantha, Carthamus palaestinus* and *Carthamus turkestanicus*, and further includes all plant cultivars and varieties belonging to the aforementioned.

"*Prunus*", as used herein, refers to a plant belonging to the biological genus *Prunus*, including any species belonging to the subgenus *Amygdalis, Prunus, Cerasus, Lithocerasus, Padus* and *Laurocerasus* and includes, without limitation, the species *Prunus dulcis*, also known as almond, and further also known as *Amygdalis communis, Amydalus communis, Prunus amygdalis (amygdalus)*, and *Prunus communis*, and further includes all plant cultivars and varieties belonging to the aforementioned.

"Oleosomes", as used herein, refer to lipid containing compartments situated within and obtainable from plant cells, comprised generally of a core of triglycerides surrounded by a monolayer of phospholipids embedded with proteins, typically oleosins, caleosins and steroleosins. Oleosomes (sometimes called "oil bodies") of different plant species have similar compositions and structures. The properties of the mixed phospholipid-protein layer at the surface of oleosomes have been found to make them particularly stable, for example, against coalescence and thermal processing. Oleosomes serve as lipid storage sites and a source of energy during seed germination. They can be recovered from the cells of reproductive organs of different plants, including, without limitation, from oleaginous seeds, nuts and fruits, using aqueous processing techniques to provide oleosome compositions.

"Personal care product" and "personal care formulation", as may be used interchangeably herein, refer to a finished product (composition or formulation) suitable for cleaning, cleansing, hydrating, maintaining, protecting, repairing, remediating, modifying the appearance (e.g. beautifying) at least a portion of the exterior surface area of the human body, including, without limitation, the skin, hair, nails, or lips, by topical application of the product to the exterior surface.

"Sunscreen active ingredient", as used herein, refers to a compound capable protecting human skin from UV radiation, i.e. radiation in the range from 200 nm to 400 nm, including UV-A radiation and/or UV-B and/or UV-C radiation, whether from sunlight or other sources of UV radiation.

By "formulating the sunscreen formulation to form a personal care product" it is meant that the sunscreen formulation is contacted (e.g. mixed) with at least one other ingredient, including, but not limited to, a diluent, excipient or carrier, and mixed, homogenized or prepared until a personal care product is formed.

It should be noted that terms of degree such as "substantially", "essentially" and "approximately" as used herein mean a reasonable amount of deviation of the modified term such that the end result is not significantly changed. These terms of degree should be construed as including a deviation of the modified term if this deviation would not negate the meaning of the term it modifies.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It will be understood that any range of values described herein is intended to specifically include any intermediate value or sub-range within the given range, and all such intermediate values and sub-ranges are individually and specifically disclosed (e.g. 1 to 5 includes 1, 1.5, 2, 2.75, 3, 3.90, 4, and 5). It is also to be understood that all numbers and fractions thereof that are modified by the term "about" are presumed to include a variation of up to a certain amount of the number to which reference is being made if the end result is not significantly changed, such as 10%, for example.

General Implementation

As hereinbefore mentioned, the present disclosure provides methods of making a sunscreen formulation. The methods of the present disclosure may be used in conjunction with a wide variety of sunscreen active ingredients, including synthetic and natural sunscreen active ingredients. Once the formulation has been constituted, the formulation may be used as an ingredient or, indeed, to form a wide variety of personal care products.

In accordance herewith it has been found, surprisingly, that sunscreen agents, when formulated with certain oleaginous ingredients at an acidic pH and in the presence of a buffering system which provides buffering capacity at such acidic pH, yields a formulation exhibiting high SPF rates, even at modest concentrations of sunscreen active agents. Furthermore, the SPF rates of personal care products prepared using the formulation of the present disclosure remain surprisingly high. When the formulation is used to prepare a personal care product, the SPF rates of the personal care products can remain relatively similar to the SPF rates of the formulation, even if the pH is increased during formulation. Therefore, in accordance with the techniques of the present disclosure, personal care products can be prepared requiring relatively small amounts of sunscreen active, yet exhibiting high SPF rates.

For example, using a formulation of the present disclosure to formulate a personal care product comprising 2.75% (w/w) of sunscreen actives octyl methoxycinnamate and avobenzone, a SPF rate of SPF 30 can be attained. By comparison, in currently commercially available sunscreen personal care products, sunscreen actives are incorporated at much higher concentrations to attain an SPF rate of 30, for example: Coppertone® Oil Free Sunscreen Lotion, SPF 30 (avobenzone 2%, homosalate 13%, octisalate 5%, octocrylene 2%, oxybenzone 4%; total 26%); Neutrogena® Ultra Sheer® Dry-touch Sunscreen, SPF 30 (avobenzone 3%, homosalate 8%, octisalate 5%, octocrylene 4%, oxybenzone 4%; total 24%), Aveeno® Active Naturals® Daily Moisturizer SPF 30 (avobenzone 3%, homosalate 12%, octisalate 5%, octocrylene 1.7%, oxybenzone 3%; total 24.7%), L'Oreal® Revitalift® Triple Action™ SPF 30 (avobenzone 3%, homosalate 5%, octisalate 5%, octocrylene 7%; total 20%) and Peter Thomas Roth Anti-Aging Defense Uber-Dry™ Sunscreen Broad Spectrum SPF 30 (avobenzone 2%, homosalate 8%, octinoxate 7.5%, octisalate 5%, oxybenzone 3.5%; total 26%).

Sunscreen products prepared using the sunscreen formulation of the present disclosure can exhibit superior sensory and aesthetic properties, cause minimal or no irritation and, importantly, offer good protection of the skin against UV-radiation. Furthermore, in embodiments hereof where natural sunscreen actives are selected, the sunscreen formulation of the present disclosure can be constituted as an all-natural formulation.

Accordingly, the present disclosure provides, in at least one embodiment, a method of preparing a sunscreen formulation comprising:
providing a sunscreen active ingredient;
preparing an oleosome suspension buffered at a pH of from about pH 3 to about pH 6, inclusive;
contacting the oleosome suspension with the sunscreen active ingredient at a pH from about pH 3 to about pH 6 to form a sunscreen formulation.

In accordance with one aspect hereof, a sunscreen active ingredient is provided or obtained. Any sunscreen active ingredient or combination of sunscreen active ingredients may be selected and used in the methods and compositions described herein. Sunscreen active ingredients can be generally classified into five groups based upon their chemical structure: amino benzoates; salicylates; cinnamates; benzophenones; and miscellaneous chemicals, which include organic and inorganic compounds, all of which may be used in accordance with the present disclosure.

In one embodiment, the sunscreen active ingredient used in accordance herewith is an amino benzoate. Example aminobenzoates include, without limitation, aminobenzoic acid, its salts, and its derivatives, such as ethyl, isobutyl, and glyceryl esters, p-dimethylaminobenzoic acid, and 4-aminobenzoic acid derivatives, including 4-(dimethylamino)-benzoic acid-2-ethylhexyl ester, 4-(diniethylamino)-benzoic acid-2-octyl ester and 4-(dimethylamino)-benzoic acid amyl ester, and the like.

In one embodiment, the sunscreen active ingredient used in accordance herewith is a cinnamate. Example cinnamates include, without limitation, cinnamic acid derivatives such as methyl and benzyl esters, α-phenyl cinnamonitrile, butyl cinnamoyl pyruvate, and the like. Examples of cinnamic acid esters include octinoxate (octyl methoxycinnamate), 4-methoxycinnamic acid propyl ester, 4-methoxycinnamic acid isoamyl ester, and octocrylene (2-ethylhexyl-2-cyano-3,3-diphenylacrylate), dihydroxycinnamic acid derivatives, trihydroxycinnamic acid derivatives, and the like.

In one embodiment, the sunscreen active ingredient used in accordance herewith is a salicylate. Exemplary salicylates include, without limitation, amyl, phenyl, benzyl, menthyl, glyceryl, and dipropylene glycol esters and the like. Specific examples of salicylic acid esters include octisalate (2-ethylhexyl salicylate), salicylic acid-4-isopropylbenzyl ester, trolamine salicylate, triethanolamine salicylate, and salicylic acid homomethyl ester.

In one embodiment, the sunscreen active ingredient used in accordance herewith is a benzophenone. Example benzophenones include, without limitation, oxybenzone, sulisobenzone, dioxybenzone, benzoresorcinol, 2,2',4,4'-tetraliydroxybenzophenone, 2,2'-dihydroxy 4,4'-dimethoxybenzophenone, octabenzone, and the like. Suitable derivatives of benzopbenone include, for example, 2-hydroxy-4-methoxybenzo-phenone, 2-hydroxy-4-methoxy-4'-methylbenzophenone, 2,2'-dihydroxy-4-methoxy-benzophenone, and the like. Other benzopbenone derivatives include sulfonic acid derivatives of benzophenones, for example 2-hydroxy-4-methoxybenzophenone-5-sulfonic acid and salts thereof.

Other suitable sunscreen active ingredients include, for example, 3-benzylidene camphor or 3-benzylidene norcamphor and derivatives thereof, such as 3-(4-methylbenzylidene)-camphor, esters of benzalmalonic acid, such as 4-methoxybenzalmalonic acid di-2-ethylhexyl ester; triazine derivatives such as, for example, 2,4,6-trianilino-(p-carbo-2'-ethyl-1'-hexyloxy)-1,3,5-triazine, and octyl triazone; methylene bis-benzotriazolyl tetramethylbutylphenol; bis-ethylhexyloxyphenol methoxyphenyl triazine; tris-biphenyl triazine; ketotricyclo(5.2.1.0)decane derivatives; 2-phenyl-benzimidazole-5-sulfonic acid and alkali metal, alkaline earth metal, ammonium, alkylammonium, alkanolammomum and glucammonium salts thereof; sulfonic acid derivatives of 3-benzylidene camphor such as, for example, 4-(2-oxo-3-bornylidenemethyl)-benzene sulfonic acid and 2-methyl-5-(2-oxo-3-bomylidene)-sulfonic acid, and salts thereof; and α-(trimethylsilyl)-ω-(trimethylsilyloxy)poly[oxy(dimethyl) silylene]-co-[oxy(methyl)(2-{4-[2,2-bis(ethoxycarbonyl)vinyl]phenoxy}-1-methyleneethyl)silylene]-co-[oxy(methyl)(2-(4-[2,2-bis(ethoxycarbonyl)vinyl]phenoxy)prop-1-enyl)silylene].

Suitable UV-A sunscreen active ingredients that may be used in accordance herewith include, without limitation, derivatives of benzoyl methane such as, for example, 1-(4'-tert-butylpheny 1)-3-(4'-methoxyphenyl)-propane-1,3-dione, 4-tert-butyl-4'-methoxydibenzoyl methane (Parsol 1789 or avobenzone), 1-phenyl-3-(4'-isopropylphenyl)-propane-1,3-dione, and disodium 2,2'-(1,4-phenylene)bis(6-sulfo-1H-benzimidazole-4-sulfonate. UV-A and UV-B sunscreen actives may also be used in the form of mixtures.

Inorganic sunscreens may also be used herein, including, without limitation, titanium dioxide, zinc oxide, iron oxide, and polymeric particles such as those of polyethylene and polyamides.

In accordance with one aspect hereof, an oleosome suspension is prepared. The oleosome suspension may be prepared from a variety of natural sources. In some embodiments, the oleosomes are prepared from plants, plant materials, or plant parts including, without limitation, pollen, spores, seed, fruit, nuts and vegetative plant organs, in which oleosomes are present. Preferably, the oleosomes employed are prepared from plant seeds, nuts or fruits. Suitable plants and plant seeds, nuts and fruits in accordance herewith are plants and plant seeds, nuts and/or fruits obtainable or obtained from the group of plant species consisting of: almond (*Prunus dulcis*), anise (*Pimpinella anisum*), avocado (*Persea* spp.), beach nut (*Fagus sylvatica*), borage (*Boragio officinalis*), Brazil nut (*Bertholletia excelsa*), candle nut (*Aleuritis tiglium*), carapa (*Carapa guineensis*), cashew nut (*Ancardium occidentale*), castor (*Ricinus communis*), coconut (*Cocus nucifera*), coriander (*Coriandrum sativum*), cottonseed (*Gossypium* spp.), crambe (*Crambe abyssinica*), *Crepis alpine*, croton (*Croton tiglium*), cucumber (*Cucumis sativus*), *Cuphea* spp., dill (*Anethum gravealis*), *Euphorbia lagascae*, evening primrose (*Oenothera biennis*), *Dimorphoteca pluvialis*, false flax (*Camolina sativa*), fennel (*Foeniculum vulgaris*), groundnut (*Arachis hypogaea*), hazelnut (*coryllus avellana*), hemp (*Cannabis sativa*), honesty plant (*Lunnaria annua*), jojoba (*Simmondsia chinensis*), kapok fruit (*Ceiba pentandra*), kukui nut (*Aleuritis moluccana*), *Lesquerella* spp., linseed/flax (*Linum usitatissimum*) including the solin genotype, lupin (*Lupinus* spp.), macademia nut (*Macademia* spp.), maize (*Zea mays*), meadow foam (*Limnanthes alba*), mustard (*Brassica* spp. and *Sinapis alba*) including their canola genotypes, olive (*Olea* spp.), oil palm (*Elaeis guineeis*), oiticia (*Licania rigida*), paw paw (*Assimina triloba*), pecan (*Juglandaceae* spp.), perilla (*Perilla frutescens*), physic nut (*Gatropha curcas*), pilinut (*Canarium ovatum*), pine nut (pine spp.), pistachio (*Pistachio vera*), pongam (*Bongamin glabra*), poppy seed (*Papaver*

*soniferum*), pumpkin (*Cucurbita pepo*), rapeseed (*Brassica* spp., including, without limitation, the canola genotype), safflower (*Carthamus tinctorius*), sesame seed (*Sesamum indicum*), soybean (*Glycine max*), squash (*Cucurbita maxima*), sal tree (*Shorea rubusha*), Stokes aster (*Stokesia laevis*), sunflower (*Helianthus annuus*), tukuma (*Astocarya* spp.); tung nut (*Aleuritis cordata*); vernonia (*Vernonia galamensis*); including any varieties, cultivars, genotypes or hybrids of any of the foregoing, and mixtures thereof.

In some embodiments, plant oleosomes are prepared from plants belonging to the genus *Carthamus*, including, without limitation, plants belonging to the plant species *Carthamus tinctorius*.

In some embodiments, plant oleosomes are prepared from plants belonging to the genus *Prunus*, including, without limitation, plants belonging to the plant species *Prunus dulcis*.

In some embodiments, plants or plant materials, such as seeds, nuts or fruits, are obtained and used as a source material whence oleosomes are extracted. A wide variety of extraction processes and techniques may be used, provided however that, such extraction processes comprise conditions sufficiently gentle and mild to not, or not substantially, destroy the oleosome structures. Thus in general, process techniques involving organic extractants, such as hexane, and high temperatures are less suitable. Suitable non-destructive extraction techniques include processes comprising (i) a comminution step, using for example stirring, milling or grinding processes and equipment, to disrupt plant tissues under conditions that do not substantially disrupt the integrity of the oleosome, and (ii) one or more aqueous extraction steps, comprising mixing of the comminuted plant material with, for example, water or an aqueous buffer, and the separation of the oleosome fraction from insoluble plant materials, for example seed hulls and cell wall materials, and plant material soluble in the aqueous phase, for example water soluble plant proteins, simple sugars and water-soluble polysaccharides, using for example centrifugation equipment. The low density fraction thus obtained from the separation process comprises an oleosome suspension, which may be a substantially pure oleosome suspension, i.e. an oleosome suspension substantially free of other plant constituents, for example an aqueous oleosome suspension comprising 10% (w/w) or less, 5% (w/w) or less, 4%, (w/w) or less, 3% (w/w) or less, 2% (w/w) or less, 1% (w/w) or less of non-oleosome plant constituents. The obtained suspension can further be described as an oil-in-water (O/W) emulsion. The oleosome suspension can further, in some embodiments, be prepared to comprise small quantities, generally constituting 5% (w/w) or less, of ingredients to protect the suspension against undesirable alterations caused by physical, chemical or biological agents, especially when the preparation is stored for longer periods of time or exposed to temperature fluctuations. Thus, for example, small quantities of preservatives, and agents enhancing the physico-chemical or sensory properties of oleosomes can be included in the oleosome suspension. Stabilizing agents are generally selected to be suitable for inclusion in a personal care product. The oleosome suspension further can contain varying amounts of water, for example more than 10% and less than 65% water by volume, more preferably more than 15% and less than 50% water by volume, and most preferably more than 20% water by volume and less than 50% water by volume, as well as minor amounts of salts. Various suitable methods for the preparation of oleosome suspensions are known to the art and are further described in for example U.S. Pat. Nos. 6,146,645, 6,183,762, 6,210,742, 6,372,234, 6,582,710, 6,596,287, 6,599,513, 6,761,914, and 8,597,694, which are all incorporated herein by reference. It is noted however the manner in which an oleosome suspension suitable in accordance with the present disclosure is obtained is without particular restrictions and may be as desired, and the present disclosure is not limited by the process used to obtain a suitable oleosome suspension.

In accordance with one aspect of the current disclosure, a buffered oleosome suspension is prepared, wherein the suspension is buffered within a pH range from about pH 3 to about pH 6, inclusive. In order to prepare a buffered oleosome suspension in accordance herewith, in one embodiment, the oleosome suspension is contacted and mixed with any buffering agent capable of buffering the oleosome suspension to obtain an oleosome suspension buffered within a pH range varying from between about pH 3 to about pH 6, inclusive.

In some embodiments, a weak acid is used to prepare an oleosome suspension buffered at a pH of from about pH 3 to about pH 6. In such embodiments, the oleosome suspension is contacted with a sufficient quantity of a weak acid, and the weak acid and oleosome suspension are mixed to obtain a buffered oleosome suspension. In accordance herewith, the buffered oleosome suspension comprises a concentration $[H^+]$ of from $10^{-3}$ to $10^{-6}$ moles per liter, at a pH of pH 3 and pH 6, respectively. In some embodiments, the weak acid is an acid comprising a pKa of from about 3 to about 6, inclusive. In some embodiments, the weak acid is an acid comprising a pKa of approximately 4. In some embodiments, the weak acid is an acid having a pKa below 3.

In some embodiments, in addition to a weak acid, a base is included in the buffered suspension. The base may be included to adjust the pH of the oleosome suspension. In some embodiments, the pH is adjusted to a pH within the range from about pH 3 to about pH 6, for example, a base may be included to adjust the pH of the oleosome suspension to about pH 3.0, 3.5, 3.6, 3.7, 3.8, 3.9, 4.0, 4.1, 4.2, 4.3, 4.4, 4.5, 4.6, 4.7, 4.8, 4.9, 5.0, 5.5 or 6.0. Such a buffered oleosome suspension comprises, at each of the respective pH's, a concentration $[H^{3O}]$ of about $10^{-3.0}$, $10^{-3.5}$, $10^{-3.6}$, $10^{-3.7}$, $10^{-3.8}$, $10^{-3.9}$, $10^{4.0}$, $10^{4.1}$, $10^{4.2}$, $10^{-4.3}$, $10^{4.4}$, $10^{-4.5}$, $10^{4.6}$, $10^{-4.7}$, $10^{4.8}$, $10^{-4.9}$, $10^{-5.0}$, $10^{-5.5}$ and $10^{-6.0}$ moles per liter, respectively. In preferred embodiments, the pH is adjusted to a pH within the range from about 4.0 to about 5.0, for example, a base may be incorporated to adjust the pH of the oleosome suspension to about 3.8, 3.9, 4.0, 4.1, 4.2, 4.3, 4.4, 4.5, 4.6, 4.7, 4.8, 4.9 or 5.0. Such a buffered oleosome suspension comprises, at each of the respective pH's, a concentration $[H^+]$ of about $10^{-4.0}$, $10^{-4.1}$, $10^{-4.2}$, $10^{-4.3}$, $10^{-4.4}$, $10^{-4.5}$, $10^{-4.6}$, $10^{-4.7}$, $10^{-4.8}$, $10^{-4.9}$, and $10^{-5.0}$, moles per liter, respectively. The optionally included base in some embodiments is a strong base.

In some embodiments, the buffering capacity (β) of the buffered oleosome suspension within the pH range of from about pH 3 to about pH 6, or within range of from about 3.75 to about 4.5, or from about 3.85 to about 4.15, is at least 0.01, at least 0.02, at least 0.03, at least, 0.04, at least 0.05, at least 0.06, at least 0.07, at least 0.08, at least 0.09, or at least 0.1, wherein the buffering capacity (β) is defined in accordance with formula (I):

$$\beta = \Delta B / \Delta pH$$

and wherein ΔB represents the molar units of acid or base added to the buffered oleosome suspension, and wherein ΔpH represents a change in pH. Thus, by way of example only, a buffered oleosome suspension having a pH of 3.5 and a buffering capacity (β) of 0.1, is a suspension to which the addition of 0.1 mole of a base would effect a pH increase of 1.0, i.e. from pH 3.5 to pH 4.5.

In some embodiments, an organic weak acid is selected from the following group of weak acids: citric acid; malic acid; acetic acid; propionic acid; formic acid; lactic acid; ascorbic acid; aconitic acid; trimesic acid; succinic acid; benzoic acid; oxalic acid; and succinic acid.

In some embodiments, a strong base is selected from the following group of bases: sodium hydroxide; potassium hydroxide; lithium hydroxide and calcium hydroxide.

In some embodiments, the following combinations of weak acids and strong bases forming a buffering system are selected: citric acid/potassium hydroxide; citric acid/calcium hydroxide; citric acid/sodium hydroxide; citric acid/lithium hydroxide; malic acid/potassium hydroxide; malic acid/calcium hydroxide; malic acid/sodium hydroxide; malic acid/lithium hydroxide; acetic acid/potassium hydroxide; acetic acid/calcium hydroxide; acetic acid/sodium hydroxide; malic acid/lithium hydroxide; propionic acid/potassium hydroxide; propionic acid/calcium hydroxide; propionic acid/sodium hydroxide; propionic acid/lithium hydroxide; formic acid/potassium hydroxide; formic acid/calcium hydroxide; formic acid/sodium hydroxide; formic acid/lithium hydroxide; lactic acid/potassium hydroxide; lactic acid/calcium hydroxide; lactic acid/sodium hydroxide; lactic acid/lithium hydroxide; ascorbic acid/potassium hydroxide, ascorbic acid/calcium hydroxide; ascorbic acid/sodium hydroxide; aconitic acid/potassium hydroxide; aconitic acid/calcium hydroxide; aconitic acid/sodium hydroxide; aconitic acid/lithium hydroxide; trimesic acid/potassium hydroxide; trimesic acid/calcium hydroxide; trimesic acid/sodium hydroxide; trimesic acid/lithium hydroxide; succinic acid/potassium hydroxide; succinic acid/calcium hydroxide; succinic acid/sodium hydroxide; succinic acid/lithium hydroxide; benzoic acid/potassium hydroxide; benzoic acid/calcium hydroxide; benzoic acid/sodium hydroxide; benzoic acid/lithium hydroxide; oxalic acid/potassium hydroxide; oxalic acid/calcium hydroxide; oxalic acid/sodium hydroxide; oxalic acid/lithium hydroxide.

In accordance herewith, the pH of the buffered oleosome suspension, if not already having a pH within the range of from about pH 3 to about pH 6, is adjusted to a pH of from about pH 3 to about pH 6, and contacted with one or more sunscreen active ingredients and mixed, homogenized or prepared to form a sunscreen formulation. In some embodiments, the pH of the buffered oleosome suspension is adjusted to be in a range from about pH 3.8 to pH 4.1. The operational conditions and techniques can vary but generally involve gentle mixing or stirring of the suspension using a mixer or a stirrer, at temperatures ranging from about 4° C. about 60° C., or from about room temperature to about 50° C. Thus, for example, the sunscreen active may be mixed with the oleosome suspension at room temperature (22±3° C.), or at a higher temperature, for example 45° C., and processes conducted under such conditions, relative to each other, may be referred to as cold and hot processes.

Thereafter, in some embodiments, the formulation can be incubated at a temperature which may range from about 4° C. to about 60° C., for at least 1 day, at least 2 days, at least 3 days, at least 4 days, at least 5 days, at least 6 days, at least 7 days, inclusive, or for a period of 1 to 2 weeks to allow the formulation to equilibrate.

The concentration of the sunscreen active ingredient may vary but generally constitutes no more than 20% (w/w), no more than 15% (w/w), no more than 10% (w/w), no more than 5% (w/w), no more than 3% (w/w), or no more than 2% (w/w) of the sunscreen formulation. Furthermore, the concentration of the sunscreen active agent in the sunscreen formulation may be optimized or adjusted, for example by preparing a plurality of sample formulations, each including a different sunscreen ingredient concentration, applying each sample to, for example an area of skin of a test subject, and evaluating the application for example with respect to for example UV-radiation protection. Then, a concentration of sunscreen and a sunscreen formulation may be selected that provides the most desirable effect.

In some embodiments, the sunscreen formulation prepared in accordance with the present disclosure comprises an oleosome suspension, a sunscreen active ingredient, one or more buffering agents and water, buffered to a pH from about pH 3 to about pH 6, which together constitute at least 90% (w/w), at least 95% (w/w), at least 96% (w/w), at least 97% (w/w), at least 98% (w/w), or at least 99% (w/w) of the sunscreen formulation.

The present disclosure further provides, in at least one embodiment, a sunscreen formulation buffered to a pH from about pH 3 to about pH 6, inclusive, comprising or consisting of a sunscreen active ingredient and an oleosome suspension. In some embodiments, the sunscreen formulation of the present disclosure comprises an oleosome suspension, a sunscreen active ingredient, one or more buffering agents and water, buffered at a pH from about pH 3 to about pH 6, inclusive, which together constitute at least 90% (w/w), at least 95% (w/w), at least 96% (w/w), at least 97% (w/w), at least 98% (w/w), or at least 99% (w/w) of the sunscreen formulation. As hereinbefore noted, in some embodiments, the sunscreen formulation may include small amounts of additional ingredients, such as preservative agents.

The sunscreen formulation of the present disclosure is further characterized by comprising oleosomes wherein the sunscreen active agents are generally associated with the protein-associated phospholipid membrane. Without wishing to be bound by theory, the inventors believe that the association of the sunscreen active agents with the protein/phospholipid membrane minimizes the ability of the sunscreen active agents to detract from the aesthetics of personal care products formulated using the formulation, and limits skin or eye irritation caused by the sunscreen active agents, while at the same time providing good protection against UV-radiation.

The sunscreen formulation of the present disclosure can comprise a wide range of SPF rates. In some embodiments, the SPF rate of the sunscreen formulation is at least SPF 2. In some embodiments, the SPF rate of the sunscreen formulation is at least SPF 5. In some embodiments, the SPF rate of the sunscreen formulation is at least SPF 10. In some embodiments, the SPF rate of the sunscreen formulation is at least SPF 15. In some embodiments, the SPF rate of the sunscreen formulation is at least SPF 20. In some embodiments, the SPF rate of the sunscreen formulation is at least SPF 25. In some embodiments, the SPF rate of the sunscreen formulation is at least SPF 26. In some embodiments, the SPF rate of the sunscreen formulation is at least SPF 27. In some embodiments, the SPF rate of the sunscreen formulation is at least SPF 28. In some embodiments, the SPF rate of the sunscreen formulation is at least SPF 29. In some embodiments, the SPF rate of the sunscreen formulation is at least SPF 30. In some embodiments, the SPF rate of the sunscreen formulation is at least SPF 35. In some embodiments, the SPF rate of the sunscreen formulation is at least SPF 40. In some embodiments, the SPF rate of the sunscreen formulation is at least SPF 50. In some embodiments, the SPF rate of the sunscreen formulation is at least SPF 60. In some embodiments, the SPF rate of the sunscreen formulation is at least SPF 70. In some embodiments, the SPF rate of the sunscreen formulation is at least SPF 80.

In accordance with one aspect of the present disclosure, the sunscreen formulation can be used to prepare a personal care product. Accordingly, the present disclosure provides, in at least one embodiment, a method of preparing a personal care product comprising a sunscreen active ingredient, the method comprising:
providing a sunscreen formulation buffered to a pH from about pH 3 to about pH 6 comprising a sunscreen active ingredient and an oleosome suspension;
formulating the sunscreen formulation with at least one ingredient suitable for the preparation of a personal care product to form a personal care product comprising a sunscreen active ingredient.

The present disclosure further provides, in at least one embodiment, a method of preparing a personal care product comprising a sunscreen active ingredient, the method comprising:
providing a sunscreen active ingredient;
preparing an oleosome suspension buffered to a pH of about pH 3 to about pH 6;
contacting the oleosome suspension with the sunscreen active ingredient to form a sunscreen formulation; and
formulating the sunscreen formulation with at least one ingredient suitable for the preparation of a personal care product to form a personal care product comprising a sunscreen active ingredient.

The present disclosure further provides, in at least one embodiment a use of a sunscreen formulation buffered to a pH from about pH 3 to about pH 6 comprising or consisting of a sunscreen active ingredient and an oleosome suspension to prepare a personal care product.

In some embodiments, the sunscreen formulation is contacted with at least one other ingredient suitable for use in a personal care product, notably a diluent, carrier or excipient. The sunscreen formulation and diluent, carrier or excipient are mixed, homogenized or prepared, preferably until a homogenous mixture of the diluent, carrier or excipient and sunscreen formulation is formed, wherein such mixture is suitable for use as a personal care product. The diluent, carrier or excipient may be any suitable diluent, carrier or excipient, and in one embodiment is a diluent, carrier or excipient not endogenously present in the seed used to prepare the oleosome suspension, or in another embodiment, a mixture suitable for the preparation of a personal care product. Furthermore, the diluent, carrier or excipient may be provided in any form, including, for example, as a solution, suspension, gel, liquid, solid, powder, or crystal. The quantity of the diluent, carrier or excipient may vary and depends on the type of personal care formulation that is prepared. Typically, a plurality of ingredients is provided, for example at least 2, 3, 4, 5, 6, 7, 8, 9, 10 or more ingredients, in addition to the sunscreen formulation, to prepare the personal care product. In embodiments hereof that include a plurality of ingredients, such ingredients may be mixed sequentially or simultaneously.

In some embodiments, a formulation suitable for inclusion in a personal care product comprising a mixture of ingredients is pre-formed, and the sunscreen formulation is separately provided and incorporated in the pre-formed ingredient mixture.

In some embodiments, the sunscreen formulation is incorporated during formulation. In such embodiments, the sunscreen formulation may be added separately or the sunscreen formulation may be incorporated together with one or more other compounds.

The final concentration of the sunscreen formulation in the personal care product may vary. In some embodiments, the sunscreen formulation comprises at least 0.1% (w/w) or about 0.1% (w/w) of the personal care product. In other embodiments, the sunscreen formulation or extract comprises at least 0.5% or about 0.5% (w/w), at least 1% or about 1% (w/w), at least 2% or about 2% (w/w), at least 5% or about 5% (w/w), at least 10% or about 10% (w/w), at least 20% or about 20% (w/w), or at least 30% or about 30% (w/w), inclusive of the personal care product. The concentration sunscreen formulation may be optimized or adjusted, for example by preparing a plurality of sample formulations, each including a different sunscreen formulation concentration, applying each sample to, for example an area of skin of a test subject, and evaluating the application for example with respect to for example UV-radiation protection. Then, a concentration of sunscreen formulation may be selected that provides the most desirable effect.

In accordance herewith, the personal care product may comprise a diluent, carrier or excipient suitable for preparing a personal care product. In some embodiments, a mixture of two or more diluents, carriers or excipients is included in the product.

In some embodiments, the diluent, carrier or excipient incorporated in the personal care products of the present disclosure are natural ingredients. In view of the fact that the oleosome suspension is a natural composition, in one embodiment, the personal care product may be formulated using only natural sunscreen active ingredients, diluents, carriers or excipients, thus providing a natural personal care product.

In some embodiments, the diluent, carrier or excipient incorporated in the personal care products of the present disclosure are synthetic ingredients.

Some optional excipients are described below in relation to personal care product formulation techniques.

In some embodiments, excipients incorporated in the personal care formulations are pH-modulating agents. In some embodiments, the pH-modulating agent is a base. In some embodiments, the pH-modulating agent is a base capable of increasing the pH to at least pH 5.5, from about pH 5.5 to about pH 6.0, from about pH 6.0 to about pH 6.5, from about pH 6.5 to about pH 7.0, from about pH 7.0 to about pH 7.5, from about pH 7.5 to about pH 8.0, or from about pH 8.0 to about pH 8.5. In accordance herewith, the modulation of the pH has no or limited impact on the SPF rate, relative to the SPF rate of the sunscreen formulation, even if the pH is modulated outside of the range of the buffering capacity of the buffering system. In some embodiments, adjustment of the pH within the range from about pH 5.5 to about pH 8.0, results in a reduction of the SPF rate, relative to the SPF rate of the sunscreen formulation, of no more than 9 SPF units, no more than 8 SPF units, no more than 7 SPF units, no more than 6 SPF units, no more than 5 SPF units, no more than 4, SPF units, no more than 3 SPF units, no more than 2 SPF units, or no more than 1 SPF unit. In some embodiments, adjustment of the pH by no more than 1 pH unit, results in a reduction of the SPF rate, relative to the SPF rate of the sunscreen formulation, of no more than 4 SPF units, no more than 3 SPF units, no more than 2 SPF units, or no more than 1 SPF unit. pH-adjusting agents that may be used in accordance herewith include, for example, NaOH or KOH.

In some embodiments, excipients incorporated in the personal care formulations of the present disclosure are surface active agents, including, for example, cationic surfactants, including, for example, natural cationic surfactants, such as brassicyl isoleucinate esylate; and/or synthetic cationic surfactants, such as cetrimonium chloride and behentrimonium, chloride; including further, for example, anionic surfactants, including, for example, natural anionic surfactants, such as sodium coco-sulfate; and/or synthetic anionic surfactants, such as sodium laureth sulfate; including further, for example, non-ionic surfactants, including for example, natural non-ionic surfactants, such as sorbitan olivate or sorbitan oleate; and/or synthetic non-ionic surfactants, such as polysorbate 20 and PEG-100 stearate; and including, still further, zwitterionic surfactants, including, for example, natural zwitterionic surfactants, such as decyl glucoside or lauryl glucoside; and/or synthetic zwitterionic surfactants, such as sodium cocoamphoacetate.

In some embodiments, excipients incorporated in the personal care formulations of the present disclosure are moisturizers. In some embodiments, the moisturizers are natural compounds, including, for example, glycerin, sodium PCA, honey, or *Aloe barbadensis* leaf extract. In other embodiments, the moisturizers are synthetic compounds, including, for example, propylene glycol.

In some embodiments, excipients incorporated included in the personal care formulations of the present disclosure are emollients, including in some embodiments, oils, waxes, lipids or other water insoluble compounds. It is noted that oils and lipids may be incorporated in the formulations of the present disclosure by using exogenous oils and lipids. In some embodiments, emollients that may be included in the personal care products of the present disclosure are natural compounds, including, for example, *Brassica* alcohol, cetyl alcohol, shea butter, safflower oil, sunflower oil, oleyl lactate, dicaprylyl ether, beeswax, carnauba wax; and/or synthetic compounds, including, for example, dimethicone, cyclopentasiloxane or $C_{12-15}$ alkyl benzoate.

In some embodiments, excipients incorporated in the personal care formulations of the present disclosure are viscosity-modulating agents. In some embodiments, the viscosity modulating agents are natural compounds, including, for example, xanthan gum, carrageenan gum, *sclerotium* gum, *Brassica* alcohol, cellulose or cellulose derivatives. In other embodiments, the viscosity-modulating agents are synthetic agents, including, for example, carbomer, sodium acrylate copolymer or cetyl alcohol In some embodiments, excipients incorporated in the personal care formulation include chelating agents. In some embodiments, the chelating agents are natural chelating agents, such as sodium gluconate. In other embodiments, the chelating agents are synthetic chelating agents, such as disodium EDTA.

In some embodiments, excipients incorporated in the personal care formulations of the present disclosure are active ingredients, in addition to the sunscreen active ingredient. In some embodiments, the active ingredients are natural active ingredients, including, for example, bisabolol, shea butter unsaponifiables, tocopherol, or rosemary extract. In other embodiments, the active ingredients are synthetic active ingredients including for example, palmitoyl tetrapeptide-7 or polyquaternium-10.

The final concentrations of the diluents, excipients and/or carriers comprising the personal care formulations, the pH of the personal care formulations, the viscosity of the personal care formulations, and other chemical and physicochemical properties of the personal care formulations of the present disclosure, and the manner in which the personal care formulations are constituted may vary substantially depending on the desired use and performance characteristics of the personal care formulation. Those of skill in the art will be familiar with a variety of different methodologies and techniques, for example, heating methodologies, stirring or mixing techniques, pH adjustment techniques, viscosity adjustment methodologies, and the like, all of which may be used, adjusted and/or optimized in to prepare suitable personal care formulations.

The sunscreen formulation in accordance with the present disclosure may be used to prepare personal care products intended to provide protection against UV-radiation whether solar UV-radiation or from artificial UV-radiation sources, such as a UV-radiation emitting sun-tanning device. The personal care products formulated in accordance with the present disclosure can comprise a wide range of SPF rates. In some embodiments, the SPF rate of the personal care product is at least SPF 2. In some embodiments, the SPF rate of the personal care product is at least SPF 5. In some embodiments, the SPF rate of the personal care product is at least SPF 10. In some embodiments, the SPF rate of the personal care product is at least SPF 15. In some embodiments, the SPF rate of the personal care product is at least SPF 20. In some embodiments, the SPF rate of the personal care product is at least SPF 25. In some embodiments, the SPF rate of the personal care product is at least SPF 30. In some embodiments, the SPF rate of the personal care product is at least SPF 35. In some embodiments, the SPF rate of the personal care product is at least SPF 40. In some embodiments, the SPF rate of the personal care product is at least SPF 45. In some embodiments, the SPF rate of the personal care product is at least SPF 50. In some embodiments, the SPF rate of the personal care product is at least SPF 60. In some embodiments, the SPF rate of the personal care product is at least SPF 70. In some embodiments, the SPF rate of the personal care product is at least SPF 80.

In addition to providing protection against UV-radiation, the personal care products prepared in accordance with the present disclosure, in some embodiments, can provide a wide variety of different uses, including a specific treatment of the exterior of the human body, including, for example, prevention or treatment of changes to the exterior surface area of the human body, such as skin changes as result of skin aging, such as wrinkles or skin blotches.

In some embodiments, a personal care product prepared in accordance with the present disclosure is a skin care formulation, including without limitation a skin cream, a facial cream, a skin cleanser, a day cream, a skin toner, a lotion, a facial mask, an anti-aging cream, a an anti-wrinkle cream, a cold weather cream, a foot cream, or a hand cream.

In some embodiments, a personal care product prepared in accordance with the present disclosure, is a bath and body formulation, including a body wash, a bar soap, a bath gel, or a shower gel.

In some embodiments, a personal care product prepared in accordance with the present disclosure is a hair care formulation, including, without limitation, a shampoo, a conditioner, a hair dye, a hair coloring formulation, a hair lightening formulation or a hair bleaching formulation.

In some embodiments, a personal care product prepared in accordance with the present disclosure is a lip care product, including a lip balm, lip moisturizer, lip conditioner, or lipstick.

In some embodiments, a personal care formulation is a make-up formulation, including, for example, a foundation, a mascara, a blush, bronzer, eye shadow, a nail polish or a make-up remover.

The above disclosure generally describes various aspects of methods and compositions of the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present invention.

EXAMPLES

Example 1—Preparation of an Oleosome-Based Sunscreen Formulation Comprising Octyl Methoxycinnamate and Avobenzone (Hot Process)

A safflower oleosome suspension was prepared by isolating an oleosome fraction from mature safflower seeds using an aqueous seed extraction process. The oleosome preparation was preserved using Geogard Ultra® (gluconolactone, sodium benzoate, calcium gluconate) (Lonza Group Ltd., Basel, CH). A total of 11.5 gram of the preserved oleosome suspension was buffered by mixing the suspension with a sufficient quantity of a citrate sodium hydroxide buffering system at 100 rpm and 45° C. to adjust the pH of the suspension to 4.0. The buffered oleosome suspension comprised 96.38% (w/w) oleosomes, 1.97% (w/w) Geogard Ultra®, 0.86% (w/w) citrate (anhydrous) and 0.79% (w/w) NaOH (10N). To the buffered oleosome suspension was added 2 g of a first sunscreen active ingredient octyl methoxycinnamate, and the suspension was mixed at 400 rpm and 45° C. for 20 minutes. Thereafter 0.75 g of a second sunscreen active ingredient, avobenzone (preheated at 45° C.) together with 2.7 g of a solubilizing agent Finsolv® PG-22 dipropylene glycol dibenzoate) (Innospec Performance Chem., Salsbury, N.C. US), was added to the system, and the system was mixed at 400 rpm and 45° C. for 20 minutes. The system was then incubated at 45° C. for 24 hours to equilibrate the system and obtain an oleosome-based sunscreen formulation buffered at pH 4.0, comprising octyl methoxycinnamate and avobenzone.

Example 2—Preparation of an Oleosome-Based Sunscreen Formulation Comprising Octyl Methoxycinnamate and Avobenzone (Cold Process)

A safflower oleosome suspension was prepared by isolating an oleosome fraction from mature safflower seeds using an aqueous seed extraction process. A total of 11.5 gram of the preserved (using Geogard Ultra®) oleosome suspension was buffered by mixing the suspension with a sufficient quantity of a citrate sodium hydroxide buffering system at 100 rpm to adjust the pH of the suspension to 4.5 (practically, pH 4-5 with varying NaOH amount). The buffered oleosome suspension comprised 96.21% (w/w) oleosomes, 1.97% (w/w) Geogard Ultra®, 0.85% (w/w) citrate (anhydrous) and 0.97% (w/w) NaOH (10N). To the buffered oleosome suspension was added 2 g of a first sunscreen active ingredient octyl methoxycinnamate, and the suspension was mixed at 400 rpm for 20 minutes. Thereafter 0.75 g of a second sunscreen active ingredient, avobenzone together with 2.7 g of a solubilizing agent Finsolv® PG-22 (preheated at 45° C. to disperse it into the system), was added to the system, and the system was mixed at 400 rpm for 20 minutes. The system obtains an oleosome-based sunscreen formulation buffered at pH 4.5 (pH 4.0-5.0), comprising octyl methoxycinnamate and avobenzone. All process was carried out at room temperature (23° C.±2° C.).

Example 3—Preparation of a Personal Care Product Comprising an Oleosome-Based Sunscreen Formulation (Hot Process)

In order to prepare a finished personal care product, to the oleosome-based sunscreen formulation of Example 1, water was added to a total mass of 97.2 g under mixing conditions at 650 rpm and 45° C. Thereafter included were: 1 g of liquid Germall Plus® (diazolidinyl urea, iodopropynyl butylcarbamate) (Lotioncrafter LLC, Eastsound, Wash. US), 0.3 g of fragrance and 1.5 g of Aristoflex® AVC (ammonium acryloyldimethyltaurate/vp copolymer) (Clariant Int'l Ltd., Muttenz, CH), and the resulting mixture was mixed with an anchor mixer at 140 rpm for 40 mins at 45° C. Thereafter the pH was adjusted to 5.75-6.0, and the finished personal care product was aged at room temperature for 7 days in the sealed dark container until SPF rate determination.

Example 4—Preparation of a Personal Care Product Comprising an Oleosome-Based Sunscreen Formulation (Cold Process)

In order to prepare a finished personal care product, to the oleosome-based sunscreen formulation of Example 2 water was added to a total mass of 97.2 g under mixing conditions at 700 rpm at room temperature (23° C.±2° C.). Thereafter included were: 1 g of liquid Germall Plus®, 0.3 g of fragrance and 1.5 g of Aristoflex® AVC, and the resulting mixture was mixed with an anchor mixer at 140 rpm for 40 mins. Then the pH was adjusted to 5.5-6.0 for SPF rate measurement.

Example 5—Measurement of SPF Rates of an Oleosome-Based Sunscreen Formulation and a Personal Care Formulation as a Function of pH (without any Final pH Adjustment)

Various aliquots of oleosome-based sunscreen formulation were prepared as described in Example 1, except that for each aliquot the pH was adjusted using NaOH (10N) to a different pH as follows: pH 3.00, 3.50, 3.70, 3.85, 3.95, 4.0, 4.15, 4.25, 4.5, 5, 6, 7, 8, 9 and 10.

Figure 3:
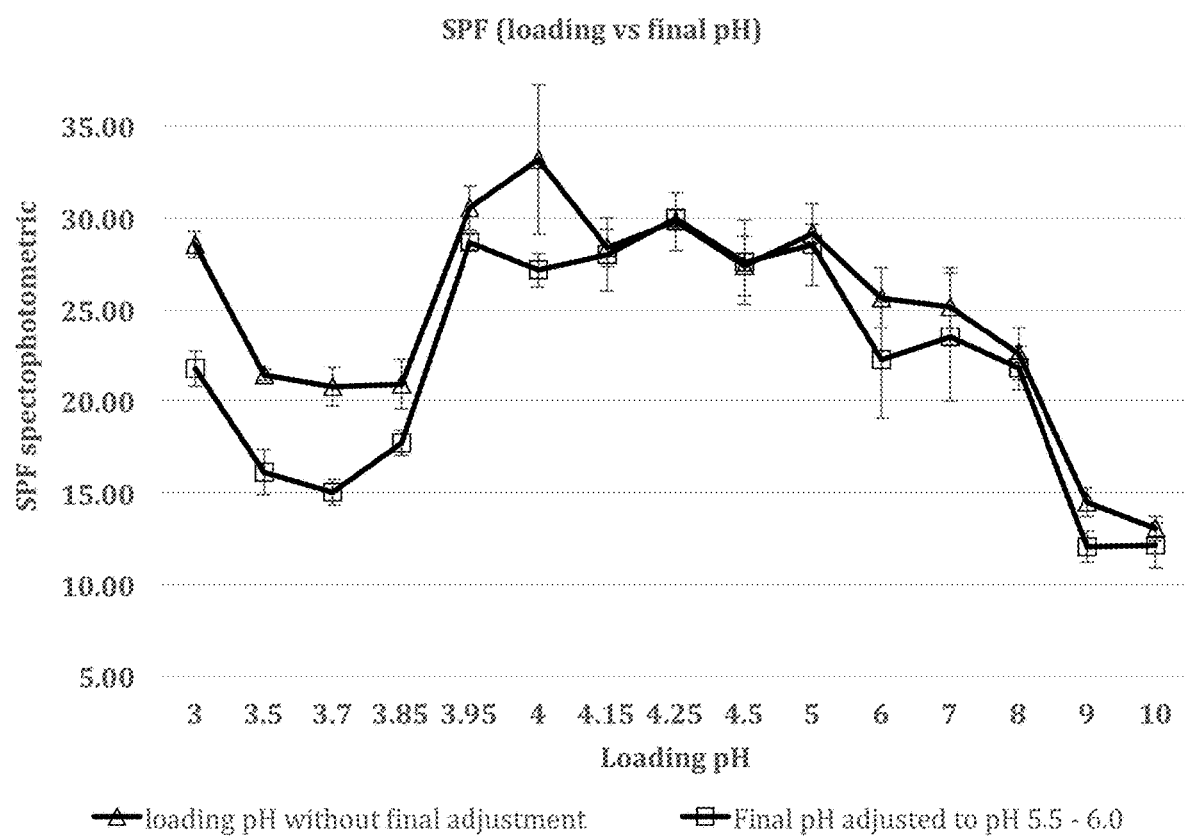
FIG. 3 is another graph representing certain results obtained in the making and using of an embodiment of a sunscreen formulation of the present disclosure and represents a combination of the graphs shown in FIG. 1 and FIG. 2.

Thereafter, each aliquot was used to prepare a finished personal care product as described in Example 3, except that the pH was not adjusted, and Aristoflex AVC was not added. The SPF rate of each finished personal care product was determined using the spectrophotometric method further described in Example 8 below. The pH of the personal care formulation was also determined while homogeneous mixing at 700 rpm. The results of the measurements of the SPF rates of the oleosome-based formulation in the finished personal care product are shown in Table 1 below and in FIG. 1 and FIG. 3 (line with triangles).

TABLE 1

Spectrophotometric SPF rates and pH change over the broad loading pH range in unbuffered system (no pH adjustment).
pH (average of duplicates)

| Initial pH | 3.00 | 3.50 | 3.70 | 3.85 | 3.95 | 4.00 | 4.15 | 4.25 | 4.50 | 5.00 | 6.00 | 7.00 | 8.00 | 9.00 | 10.00 |
|---|---|---|---|---|---|---|---|---|---|---|---|---|---|---|---|
| Final pH | 3.26 | 4.74 | 3.80 | 3.93 | 3.95 | 4.01 | 4.13 | 4.24 | 4.21 | 4.68 | 5.47 | 6.00 | 7.24 | 7.63 | 7.75 |
| Final SPF | 28.5 | 21.4 | 20.8 | 20.9 | 30.5 | 33.2 | 28.4 | 29.8 | 27.4 | 29.1 | 25.6 | 25.1 | 25.6 | 14.5 | 13.1 |

Shown in Table 1 are the pH of the oleosome-based sunscreen formulation (top row), the pH of the personal care product and the SPF rate of the personal care product. Shown in FIG. 1 is a plot of the SPF rate as a function of the initial pH (Table 1, top row).

Example 6—Measurement of SPF Rates of an Oleosome-Based Formulation and a Personal Care Formulation as a Function of pH (with a Final pH Adjustment Between 5.5 and 6.0)

Various formulations of oleosome-based sunscreen ingredient preparations were prepared as described in Example 1, except that for each formulation the pH was adjusted using NaOH (10N) to a different pH as follows: pH 3.00, 3.50, 3.70, 3.85, 3.95, 4.0, 4.15, 4.25, 4.5, 5, 6, 7, 8, 9 and 10.

Figure 2:
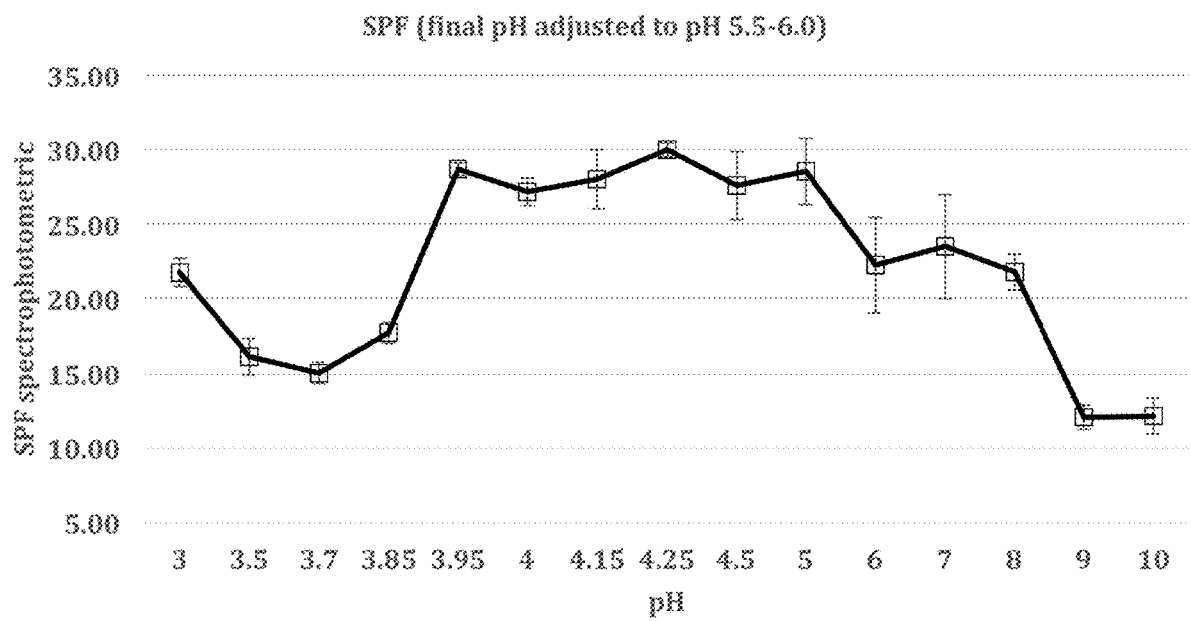
FIG. 2 is another graph representing certain results obtained in the making and using an embodiment of a sunscreen formulation of the present disclosure. The graph shows SPF-rates of a personal care product comprising a sunscreen formulation and formulated to a final pH of 5.5 to pH 6.0, as a function of pH of the sunscreen formulation.

Thereafter each formulation was used to prepare a finished personal care product as described in Example 3, except that the pH was adjusted to between 5.5 and 6.0 in the absence of Aristoflex AVC. The SPF rate of each finished personal care product was determined using the spectrophotometric method further described in Example 8 below. The pH of the personal care formulation was also determined while homogeneous mixing at 700 rpm. The results of the measurements of the SPF rates of the oleosome-based formulation in the finished personal care product are shown in Table 2 below and in FIG. 2 and FIG. 3 (line with circles).

Example 7—In Vivo SPF Testing of Non-Buffered Samples Compared to Samples with a Buffering System In order to demonstrate the importance of the pH buffering system, sunscreen actives were formulated with an unbuffered Hydresia® SF2 oleosome system (Botaneco, Calgary, Alberta, CA) as per Table 3 below, and the in vivo SPF rates were tested at AMA Laboratory (New City, N.Y., US). All samples tested had equal amounts of octyl methoxycinnamate and avobenzone.

TABLE 3

In vivo test results from the AMA laboratory.

| SPF | Sample Description |
|---|---|
| 12.45 | Non-buffered (hot process, example 1 and 3) |
| 15 | Non-buffered (hot process, example 1 and 3) |
| 15 | Non-buffered (hot process, example 1 and 3) |
| 12.45 | Non-buffered (cold process with homogenization at 1800 rpm for 10 minutes) |
| 12.45 | Non-buffered (hot process with homogenization at 1800 rpm for 10 minutes) |
| 12.45 | Non-buffered (hot process, example 1 and 3 without incubation at 45° C.) |

TABLE 2

Spectrophotometric SPF at adjusted pH range (5.5-6.0) over the broad loading pH range in unbuffered system.
pH (average of duplicates)

| Initial pH | 3.00 | 3.50 | 3.70 | 3.85 | 3.95 | 4.00 | 4.15 | 4.25 | 4.50 | 5.00 | 6.00 | 7.00 | 8.00 | 9.00 | 10.00 |
|---|---|---|---|---|---|---|---|---|---|---|---|---|---|---|---|
| Final pH | 5.80 | 5.82 | 5.72 | 5.84 | 5.77 | 5.82 | 5.76 | 5.89 | 5.79 | 5.82 | 5.95 | 5.95 | 5.80 | 5.82 | 5.82 |
| Final SPF | 21.8 | 16.1 | 15.0 | 17.7 | 28.7 | 27.1 | 28.0 | 30.0 | 27.6 | 28.5 | 22.2 | 23.5 | 21.8 | 12.1 | 12.1 |

Shown in Table 2 are the pH of the oleosome-based sunscreen formulation (top row), the pH of the personal care product (adjusted to be between pH 5.5 and 6.0) and the SPF rate of the personal care product. Shown in FIG. 1 is a plot of the SPF rates as a function of the initial pH (Table 1, top row).

Although the SPF rates of the pH-adjusted personal care formulations are slightly lower than those observed in non-pH adjusted formulations (Table 1), following adjustment of the pH from the initial pH to a pH in the range of 5.5 to 6.0, only a very small reduction in SPF rate is observed. Especially when the oleosome-sunscreen formulation initially is buffered between pH 3.95 and 5.00, personal care products having a pH between 5.5 and 6.0 and a high SPF rate (between SPF 27.2 and SPF 30.0) can be prepared. This is a desirable attribute of the oleosome-based sunscreen formulation, as many personal care formulations are commonly formulated to a final pH within the range of pH 5.5 to pH 6.0

The in vivo SPF rates achieved with either the hot or the cold process without any pH buffering as described in Table 3 above ranges from a SPF rate of SPF 12.45 to SPF 15.

By comparison, samples prepared according to Example 1 (hot process) with a sufficient quantity of a citrate sodium hydroxide buffering system with a pH adjustment to 4.0 and formulated according to Example 3 (hot process) had an in vivo SPF rate of SPF 32.5 in a 2 subject in vivo test. Also, samples prepared according to Example 2 (cold process) with a sufficient quantity of a citrate-sodium hydroxide buffering system with a pH adjustment to 4.0 and formulated according to Example 4 (cold process) had a SPF rate of SPF 32.7 in a 5 subject in vivo test. As above, all samples tested had equal amounts of octyl methoxycinnamate and avobenzone.

The SPF rates obtained using a buffering system were at least double that of the SPF rates without any pH buffering system indicating the importance of the buffering system in an oleosome-based sunscreen formulation.

Example 8—Determination of SPF Rates Using Spectrophotometric Method

The SPF rates were determined using in-house spectrophotometric methods as initial screening tools. The methods were developed with modifications from previous reports. See: Kaur & Saraf, *In vitro sun protection factor determination of herbal oils used in cosmetics*, Pharmacognosy Res. 2(1):22-25 (2010); Sayre et al., *Comparison of in vivo and in vitro testing of sunscreening formulas*, J. Soc. Cosmet. Chem. 11:280-91 (1960); *Determination of sun protection factor (SPF) of sunscreens by ultraviolet spectroscopy*, Braz. J. Pharm. Sci. 40(3):381-385 (2004). Further confirmations were carried out by in vivo tests using FDA-approved protocols.

Example 9—Preparation of a Personal Care Product Comprising an Oleosome-Based Sunscreen Formulation (Cold Process)

Figure 4:
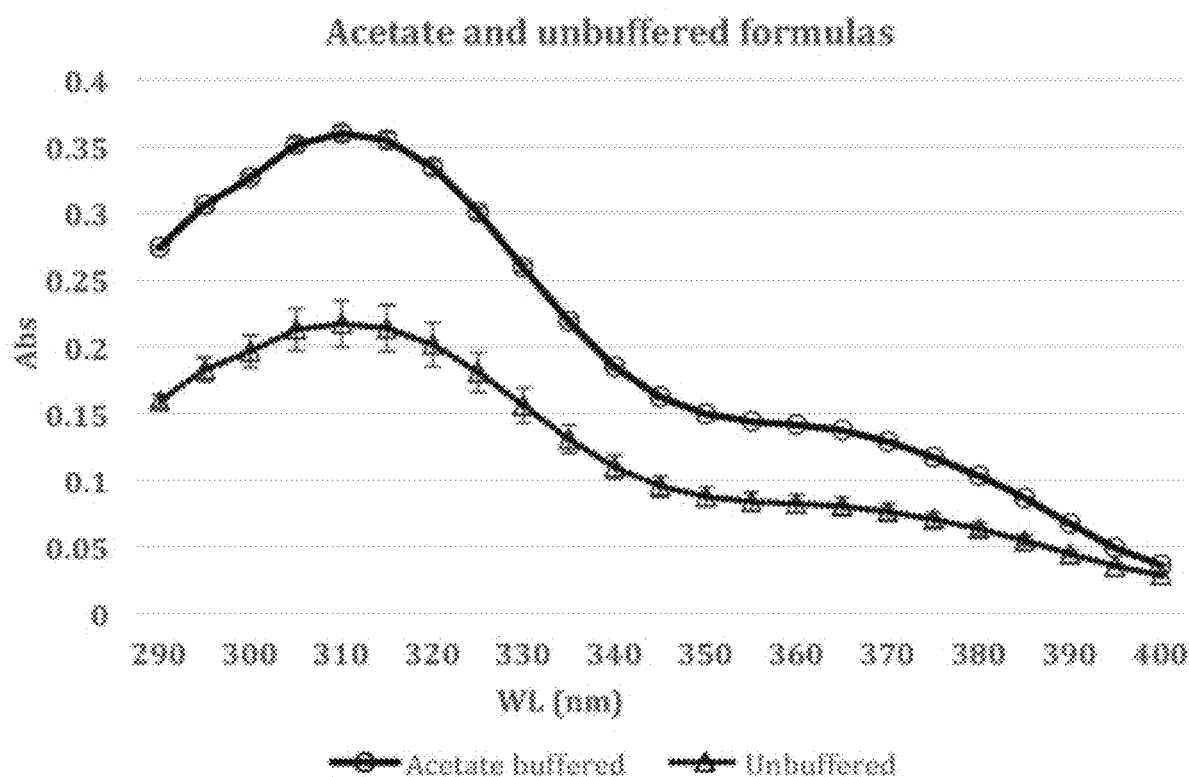
FIG. 4 is another graph representing certain results obtained in the making and using of an embodiment of a sunscreen formulation of the present disclosure. The graphs show the UV absorbance of an acetate buffered formula and an unbuffered SPF 30 formula.

An oleosome-based sunscreen formulation was prepared according to Example 2 with the exception that an acetate sodium hydroxide buffering system was used. The oleosome suspension was prepared with 1.03 g of acetate (glacial, AX0073-59, EMD Millipore) in 100 g of a preserved oleosome suspension with 0.4 g of 10N NaOH. The final pH was 4.07. The molarity of this concentrate is 169 mM. 11.7 g of this buffered oleosome suspension was used to make the finished personal care product in accordance with Example 4. In this example, the final molarity of the finished personal care product was 19.7 mM and the octyl methoxycinnamate and avobenzone were used at a level of 2% and 0.75% respectively. UV absorbance over UVA and UVB ranges by acetate buffered and unbuffered formulas are shown in the FIG. 4. Duplicated samples were prepared and the spectrophotometric SPF by unbuffered and buffered formulas demonstrated SPF 20.8 and SPF 30.2, respectively.

Example 10—Preparation of a Personal Care Product Comprising an Oleosome-Based Sunscreen Formulation (Cold Process)

Figure 5:
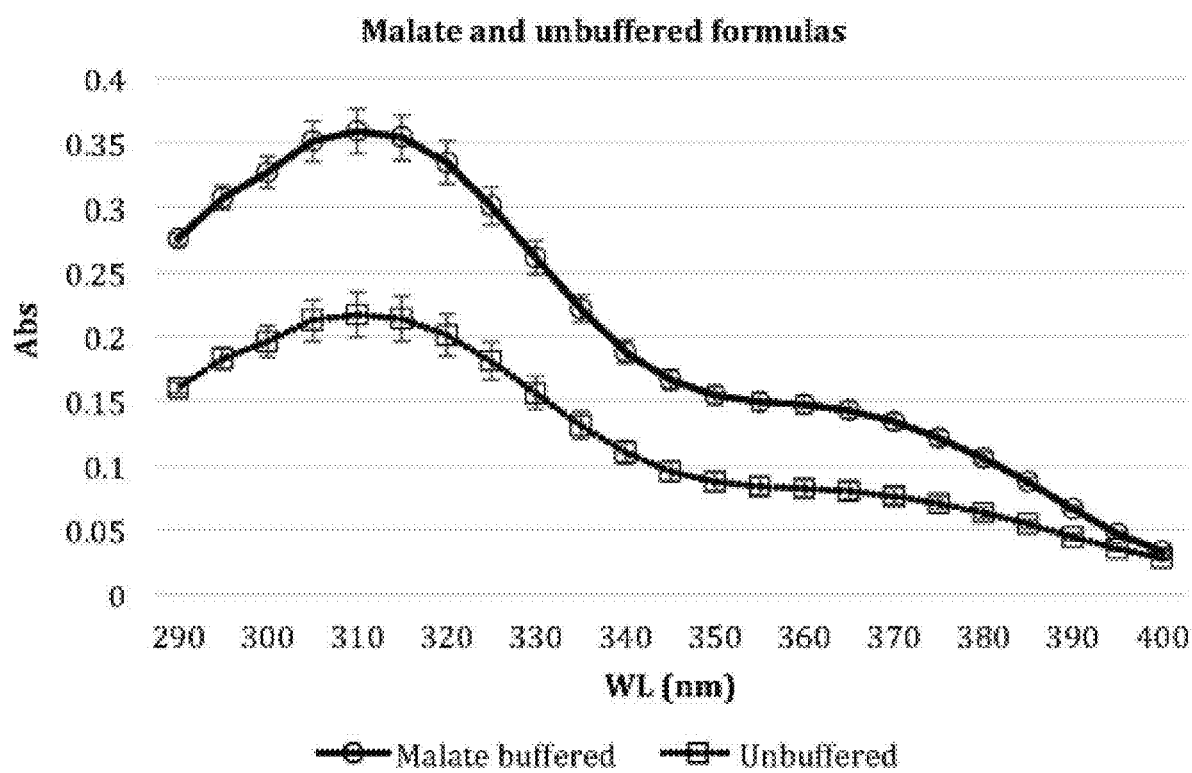
FIG. 5 is another graph representing certain results obtained in the making and using of an embodiment of a sunscreen formulation of the present disclosure. The graphs show the U V absorbance of a malate buffered formula and an unbuffered SPF 30 formula as a function of UV absorbance over UVA and UVB ranges.

An oleosome-based sunscreen formulation was prepared according to Example 2 with the exception that a malate sodium hydroxide buffering system was used. The oleosome suspension was prepared with using DL-malic acid (Alfa Aesar, A17874) at 0.75% with 98.55% of a preserved oleosome suspension and 0.7% of 10N NaOH. The final pH was 4.15. The molarity of this concentrate is 55.96 mM. 11.7 g of this buffered oleosome suspension was used to make the finished personal care product in accordance with Example 4. In this example, the octyl methoxycinnamate and avobenzone were used at a level of 2% and 0.75% respectively. UV absorbance over UVA and UVB ranges by malate buffered and unbuffered formulas are shown in the FIG. 5. Duplicated samples were prepared and the spectrophotometric SPF by unbuffered and buffered formulas demonstrated SPF 20.8 and SPF 30.2, respectively.

Example 11—Preparation of a Personal Care Product Comprising an Oleosome-Based Sunscreen Formulation (Cold Process)

Figure 6:
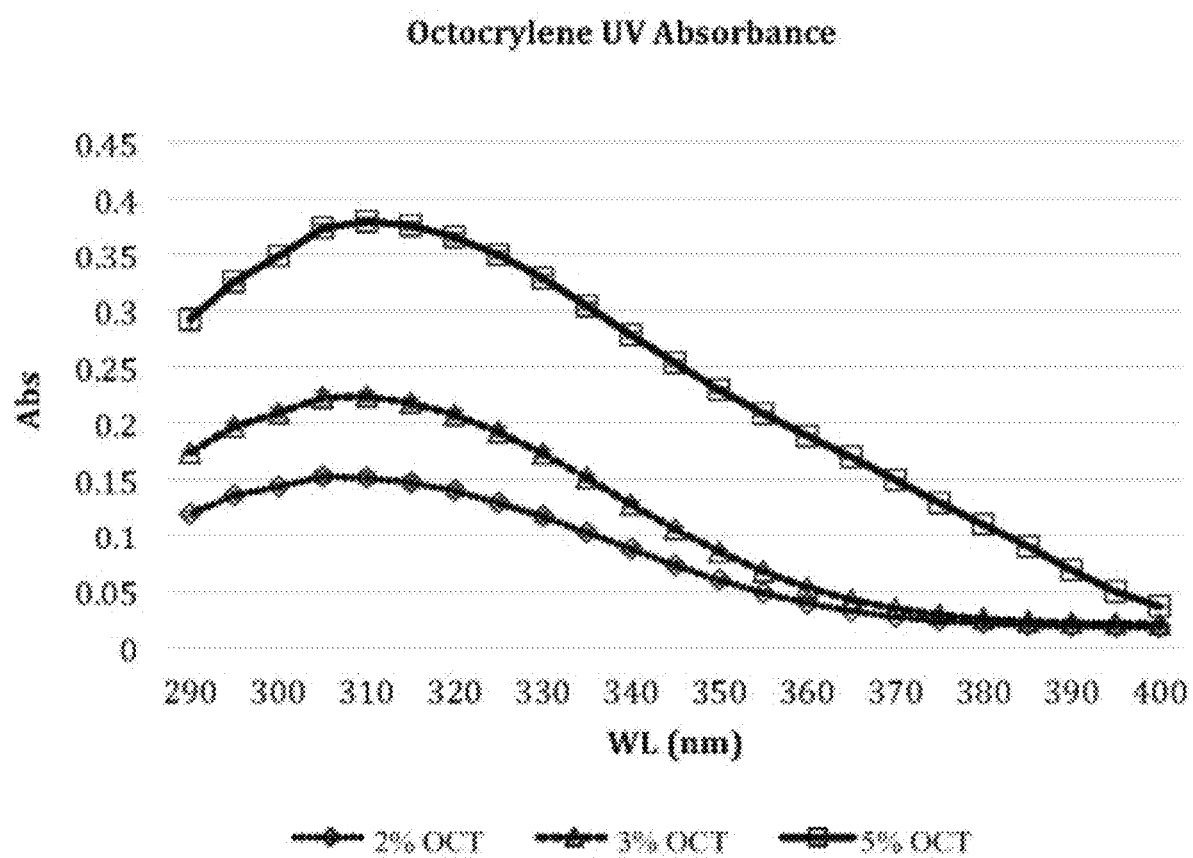
FIG. 6 is another graph representing certain results obtained in the making and using of an embodiment of a sunscreen formulation of the present disclosure. The graphs show the UV absorbance of a personal care product comprising octocrylene as a function of UV absorbance over UVA and UVB ranges.

An oleosome-based sunscreen formulation was prepared according to Example 2 at a pH of 4.2. The oleosome-based sunscreen formulation was used to make the finished personal care product in accordance with Example 4 except that Octocrylene (Escalol 597, product code: #827742, Ashland Specialty Ingredients, Del, USA) at a concentration of 2, 3 and 5% was used instead of the octyl methoxycinnamate. In this example avobenzone at 0.75% was used. The samples were prepared in duplicate. Spectrophotometric SPF rates observed for 2, 3, 5% of octocrylene were SPF 16.82, SPF 21.53, and SPF 31.69, respectively, as shown in FIG. 6. An external clinical Laboratory, AMA Laboratory (New City, N.Y., USA), confirmed the observation in 2-subject human test. A formulation at 5% OCT with 0.75% avobenzone achieved an average SPF rate of SPF 32.25 (ID#: P-2195) as shown in TABLE 4.

TABLE 4

In vivo test results from the AMA laboratory.

| SPF | Subject Number |
|---|---|
| 30.00 | 80 1093 |
| 34.50 | 88 8890 |
| 32.25 | Mean (x) |

Example 12—Preparation of a Personal Care Product Comprising an Oleosome-Based Sunscreen Formulation (Cold Process)

Figure 7:
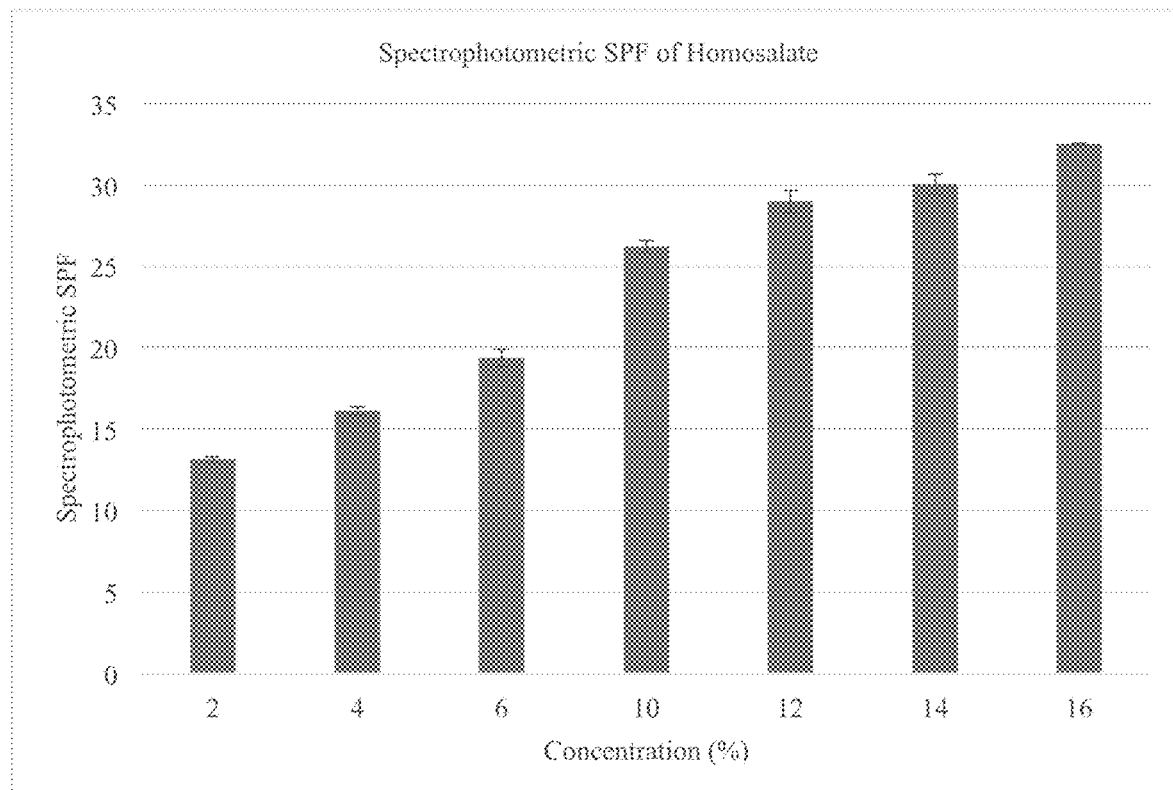
FIG. 7 is another graph representing certain results obtained in the making and using of an embodiment of a sunscreen formulation of the present disclosure. The graphs show SPF-rates of a personal care product comprising homosalate at levels of 2 to 16% as a function of UV absorbance over UVA and UVB ranges.

An oleosome-based sunscreen formulation was prepared according to Example 2 at a pH of 4.2. The oleosome-based sunscreen formulation was used to make the finished personal care product in accordance with Example 4 except homosalate (Eusolex HMS, CAS-No: 118-56-9, Merck KGaA, Germany) was used at a level of 2%, 4%, 6%, 10%, 12% and 14% in a 10% preserved oleosome suspension instead of the octyl methoxycinnamate. In this example, avobenzone was used at 0.75%. The samples were prepared in duplicate. Spectrophotometric SPF rates observed as a function of homosalate concentration are shown in FIG. 7.

Example 13—Preparation of a Personal Care Product Comprising an Oleosome-Based Sunscreen Formulation (Cold Process)

Figure 8:
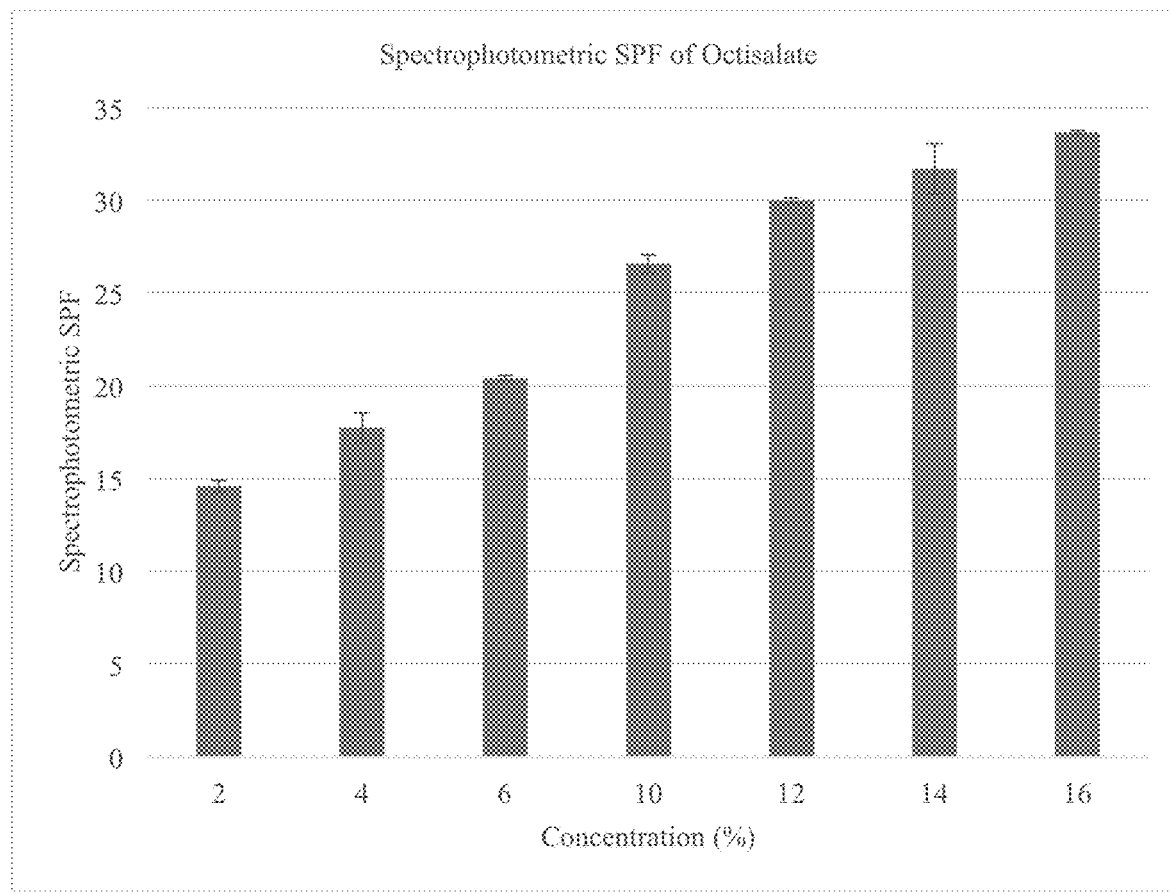
FIG. 8 is another graph representing certain results obtained in the making and using of an embodiment of a sunscreen formulation of the present disclosure. The graphs show SPF-rates of a personal care product comprising octisalate at levels of 2 to 16% as a function of UV absorbance over UVA and UVB ranges.

An oleosome-based sunscreen formulation was prepared according to Example 2 at a pH of 4.2. The oleosome-based sunscreen formulation was used to make the finished personal care product in accordance with Example 4 except 2, 4, 6, 10, 12, 14, and 16% of octisalate (Eusolex OS, CAS-No: 118-60-5, Merck KGaA, Germany) at 10% level of a preserved oleosome suspension were used instead of the octyl methoxycinnamate. In this example, avobenzone was used at 0.75%. The samples were prepared in duplicate. Spectrophotometric SPF rate observed as a function of octisalate concentration are shown in FIG. 8.

Example 14—Preparation of a Personal Care Product Comprising an Oleosome-Based Sunscreen Formulation (Cold Process)

Figure 9:
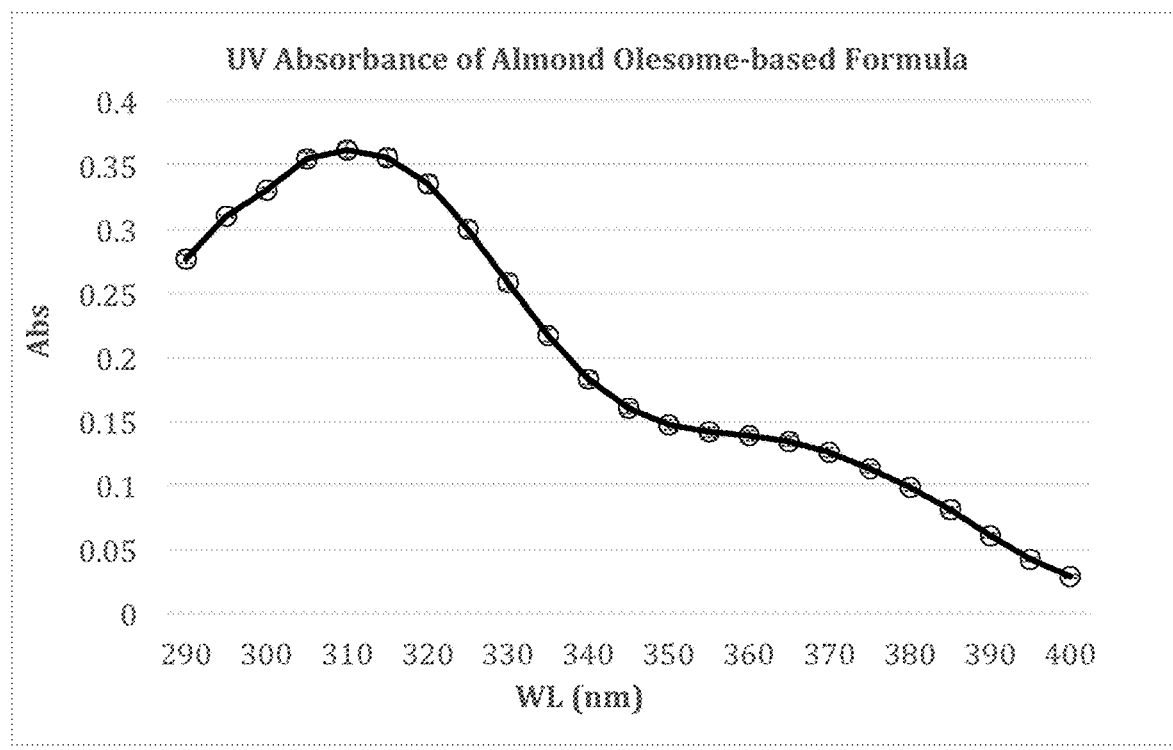
FIG. 9 is another graph representing certain results obtained in the making and using of an embodiment of a sunscreen formulation of the present disclosure. The graph shows the UV absorbance of an almond oleosome-based sunscreen formulation as a function of UV absorbance over the UVA and UVB ranges.

An oleosome-based sunscreen formulation was prepared according to Example 2 with the exception that a preserved almond oleosome suspension was used. The almond oleosome-based sunscreen formulation was buffered at pH 4.1. The almond oleosome-based sunscreen formulation was used to make the finished personal care product in accordance with Example 4. In this example, OMC was used at a concentration of 2% and avobenzone was used at a concentration of 0.75%. The samples were prepared in duplicate. The spectrophotometric SPF rate was SPF 30.4 at an UV absorbance over 290-400 nm as shown in FIG. 9.

We claim:

1. A sunscreen formulation for preparing a personal care product, the sunscreen formulation buffered to a pH from about pH 3 to about pH 6 and comprising:
    one or more sunscreen active ingredients; and
    a buffered oleosome suspension at a pH from about pH 3 to about pH 6, the buffered oleosome suspension comprising a weak acid, a strong base, and at least 90% w/w oleosomes, wherein the weak acid and the strong base form a buffering system to buffer the oleosome suspension at the pH from about pH 3 to about pH 6,
    wherein the buffering system has a buffering capacity within the pH range of from about pH 3 to about pH 6 of at least 0.01 and it is the buffering system of the oleosome suspension that buffers the sunscreen formulation to the pH from about pH 3 to about pH 6.

2. The sunscreen formulation of claim 1, wherein the weak acid comprises a pKa of from about 3 to about 6.

3. The sunscreen formulation of claim 1, wherein the weak acid is citric acid, malic acid, acetic acid, propionic acid, formic acid, lactic acid, ascorbic acid, aconitic acid, trimesic acid, succinic acid, benzoic acid, oxalic acid, or succinic acid.

4. The sunscreen formulation of claim 1, wherein the strong base is sodium hydroxide, potassium hydroxide, lithium hydroxide, or calcium hydroxide.

5. The sunscreen formulation of claim 1, wherein the weak acid/strong base of the buffering system is citric acid/potassium hydroxide; citric acid/calcium hydroxide; citric acid/sodium hydroxide; citric acid/lithium hydroxide; malic acid/potassium hydroxide; malic acid/calcium hydroxide; malic acid/sodium hydroxide; malic acid/lithium hydroxide; acetic acid/potassium hydroxide; acetic acid/calcium hydroxide; acetic acid/sodium hydroxide; malic acid/lithium hydroxide; propionic acid/potassium hydroxide; propionic acid/calcium hydroxide; propionic acid/sodium hydroxide; propionic acid/lithium hydroxide; formic acid/potassium hydroxide; formic acid/calcium hydroxide; formic acid/sodium hydroxide; formic acid/lithium hydroxide; lactic acid/potassium hydroxide; lactic acid/calcium hydroxide; lactic acid/sodium hydroxide; lactic acid/lithium hydroxide; ascorbic acid/potassium hydroxide, ascorbic acid/calcium hydroxide; ascorbic acid/sodium hydroxide; aconitic acid/potassium hydroxide; aconitic acid/calcium hydroxide; aconitic acid/sodium hydroxide; aconitic acid/lithium hydroxide; trimesic acid/potassium hydroxide; trimesic acid/calcium hydroxide; trimesic acid/sodium hydroxide; trimesic acid/lithium hydroxide; succinic acid/potassium hydroxide; succinic acid/calcium hydroxide; succinic acid/sodium hydroxide; succinic acid/lithium hydroxide; benzoic acid/potassium hydroxide; benzoic acid/calcium hydroxide; benzoic acid/sodium hydroxide; benzoic acid/lithium hydroxide; oxalic acid/potassium hydroxide; oxalic acid/calcium hydroxide; oxalic acid/sodium hydroxide; or oxalic acid/lithium hydroxide.

6. The sunscreen formulation of claim 1, wherein the buffering system is a citrate-sodium hydroxide buffering system using citric acid as the weak acid and sodium hydroxide as the strong base.

7. The sunscreen formulation of claim 1, wherein the buffering system is an acetate-sodium hydroxide buffering system using acetic acid as the weak acid and sodium hydroxide as the strong base.

8. The sunscreen formulation of claim 1, wherein the buffering system is a malate-sodium hydroxide buffering system using malic acid as the weak acid and sodium hydroxide as the strong base.

9. The sunscreen formulation of claim 1, wherein the buffering capacity of the buffering system within the pH range of from about pH 3 to about pH 6 is at least 0.05.

10. The sunscreen formulation of claim 1, wherein the buffering capacity of the buffering system within the pH range of from about pH 3 to about pH 6 is at least 0.1.

11. The sunscreen formulation of claim 1, wherein the buffered oleosome suspension has a pH of from about pH 4 to about pH 5.

12. The sunscreen formulation of claim 1, wherein the buffered oleosome suspension has a pH of from about pH 3.8 to about pH 4.1.

13. The sunscreen formulation of claim 1, wherein the buffered oleosome suspension further comprises a preservative at an amount of 5% or less w/w of the buffered oleosome suspension.

14. The sunscreen formulation of claim 13, wherein the preservative comprises gluconolactone, sodium benzoate, and calcium gluconate.

15. The sunscreen formulation of claim 1, further comprising a solubilizing agent.

16. The sunscreen formulation of claim 15, wherein the solubilizing agent is dipropylene glycol dibenzoate.

17. The sunscreen formulation of claim 1, wherein the amount of the one or more sunscreen active ingredients is no more than 20% w/w of the sunscreen formulation.

18. The sunscreen formulation of claim 1, wherein the buffered oleosome suspension comprises at least 95% w/w oleosomes.

19. The sunscreen formulation of claim 18, which comprises at least 60% w/w of the oleosome suspension.

20. The sunscreen formulation of claim 18, wherein the buffered oleosome suspension further comprises a preservative and the sunscreen formulation comprises at least 65% w/w of the oleosome suspension.

21. The sunscreen formulation of claim 20, which comprises no more than 20% w/w of the one or more sunscreen active ingredients.

22. The sunscreen formulation of claim 20, which comprises at least 15% w/w of a solubilizer.

23. A personal care product comprising the sunscreen formulation of claim 1.

24. The personal care product of claim 23, wherein the personal care product is selected from the group consisting of skincare products, hair care products, bath and body wash products, lip care products, and make-up products.

* * * * *